(12) United States Patent
Miyake et al.

(10) Patent No.: US 7,446,218 B2
(45) Date of Patent: *Nov. 4, 2008

(54) PROCESS FOR PRODUCING CARBONIC ESTER

(75) Inventors: Nobuhisa Miyake, Kurashiki (JP); Tomonari Watanabe, Yamato (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 507 days.

This patent is subject to a terminal disclaimer.

(21) Appl. No.: 10/522,754

(22) PCT Filed: Aug. 6, 2003

(86) PCT No.: PCT/JP03/10004

§ 371 (c)(1),
(2), (4) Date: Jan. 28, 2005

(87) PCT Pub. No.: WO2004/014840

PCT Pub. Date: Feb. 19, 2004

(65) Prior Publication Data

US 2005/0240045 A1 Oct. 27, 2005

(30) Foreign Application Priority Data

Aug. 7, 2002 (JP) .............................. 2002-229385

(51) Int. Cl.
*C07C 69/96* (2006.01)
(52) U.S. Cl. ...................................... 558/260; 558/270
(58) Field of Classification Search .................. 558/260, 558/270
See application file for complete search history.

(56) References Cited

U.S. PATENT DOCUMENTS 5,543,546 A * 8/1996 Tsuneki et al. .............. 558/270
2005/0080274 A1 4/2005 Miyake et al.

FOREIGN PATENT DOCUMENTS

JP 2001-247519 9/2001

OTHER PUBLICATIONS

Itakura et al., 1999, CAS: 130:168016.*
Ko et al., 1995, CAS: 122:290332.*
Yamazaki et al., CAS: 90:168087.*

* cited by examiner

*Primary Examiner*—Rei-Tsang Shiao
(74) *Attorney, Agent, or Firm*—Finnegan, Henderson, Farabow, Garrett & Dunner, L.L.P.

(57) ABSTRACT

A method for producing a carbonic ester, comprising: (1) performing a reaction between an organometal compound mixture and carbon dioxide, the organometal compound mixture comprising a reactive organometal compound and an unregenerable unreactive compound derived from the reactive organometal compound, to thereby obtain a reaction mixture containing a carbonic ester, the unregenerable unreactive compound, and a regenerable metamorphic organometal compound derived from the reactive organometal compound, (2) separating the reaction mixture into a first portion containing the carbonic ester and the unregenerable unreactive compound, and a second portion containing the regenerable metamorphic organometal compound, and (3) reacting the second portion of the reaction mixture with an alcohol to form an organometal compound mixture and water and removing the water from the organometal compound mixture, the organometal compound mixture comprising a reactive organometal compound and an unregenerable unreactive compound derived from the reactive organometal compound.

15 Claims, 1 Drawing Sheet

PROCESS FOR PRODUCING CARBONIC ESTER

CROSS REFERENCE TO RELATED APPLICATIONS

This application is an national phase application based on PCT/JP2003/010004, filed Aug. 6, 2003, which claims the priority of Japanese Patent Application No. 2002-229385, filed Aug. 7, 2002, the content of both of which is incorporated herein by reference in its entirety.

BACKGROUND OF THE INVENTION

1. Field of the Invention

The present invention relates to a method for producing a carbonic ester from an organometal compound and carbon dioxide. More particularly, the present invention is concerned with a method for producing a carbonic ester, comprising the steps of: (1) performing a reaction between a first organometal compound mixture and carbon dioxide, wherein the first organometal compound mixture comprises a mixture of a reactive organometal compound having in its molecule at least two metal-oxygen-carbon linkages and an unregenerable unreactive compound which is derived from the reactive organometal compound, to thereby obtain a reaction mixture containing a carbonic ester formed by the reaction, the unregenerable unreactive compound, and a regenerable metamorphic organometal compound derived from the reactive organometal compound, (2) separating the reaction mixture into a first portion containing the carbonic ester and the unregenerable unreactive compound, and a second portion containing the regenerable metamorphic organometal compound, and (3) reacting the second portion of the reaction mixture with an alcohol to form a second organometal compound mixture and water and removing the water from the second organometal compound mixture, wherein the second organometal compound mixture comprises a mixture of a reactive organometal compound having in its molecule at least two metal-oxygen-carbon linkages and an unregenerable unreactive compound which is derived from the reactive organometal compound.

By the method of the present invention, a carbonic ester can be produced in high yield from an organometal compound having in its molecule at least two metal-oxygen-carbon linkages and carbon dioxide. One advantage of this method is that carbon dioxide has neither toxicity nor corrosiveness and is inexpensive. Further, the method of the present invention is advantageous not only in that the organometal compound after use in this method can be regenerated and recycled for reuse in the method, but also in that the unregenerable unreactive organometal compound formed in the method can be removed from the reaction system, thereby realizing an efficient and stable production of a carbonic ester. Moreover, there is no need for the use of a large amount of a dehydrating agent, thereby preventing occurrence of wastes derived from the dehydrating agent. Therefore, the method of the present invention is commercially very useful and has high commercial value.

2. Prior Art

A carbonic ester is a useful compound. For example, a carbonic ester is used as additives for various purposes, such as a gasoline additive for improving the octane number of a gasoline, and a diesel fuel additive for reducing the amount of particles in an exhaust gas generated by the burning of a diesel fuel. A carbonic ester is also used as an alkylation agent, a carbonylation agent, a solvent and the like in the field of the synthesis of organic compounds, such as polycarbonate, urethane, pharmaceuticals and agrichemicals. A carbonic ester is also used as an electrolyte for a lithium battery, a raw material for producing a lubricant oil and a raw material for producing a deoxidizer which can be used for preventing boiler pipes from rusting.

As a conventional method for producing a carbonic ester, there can be mentioned a method in which phosgene used as a carbonyl source is reacted with an alcohol, thereby producing a carbonic ester. Since phosgene used in this method is extremely harmful and highly corrosive, this method is disadvantageous in that the transportation and storage of phosgene need detailed care and, also, there is a large cost for the maintenance of production equipment and for assuring safety. Further, this method poses a problem in that it is necessary to dispose of hydrochloric acid produced as a waste by-product.

Another conventional method for producing a carbonic ester is an oxidative carbonylation method in which carbon monoxide used as a carbonyl source is reacted with an alcohol and oxygen in the presence of a catalyst, such as copper chloride, thereby producing a carbonic ester. In this method, carbon monoxide (which is extremely harmful) is used under high pressure; therefore, this method is disadvantageous in that there is a large cost for the maintenance of production equipment and for assuring safety. In addition, this method poses a problem in that a side reaction occurs, such as oxidation of carbon monoxide to form carbon dioxide. For these reasons, it has been desired to develop a safer and more efficient method for producing a carbonic ester.

In these conventional methods in which phosgene or carbon monoxide is used as a raw material, a halogen, such as chlorine, is contained in the raw material itself or in the catalyst used. Therefore, in the case of these methods, a carbonic ester obtained contains a trace amount of a halogen which cannot be completely removed by a simple purification step. When such carbonic ester is used as a gasoline additive, a light oil additive or a material for producing electronic equipment, there is a danger that the halogen contained in the carbonic ester causes corrosion of equipment. For reducing the amount of a halogen in the carbonic ester to only a trace amount, it is necessary to perform a thorough purification of the carbonic ester. For this reason, it has been desired to develop a method for producing a carbonic ester, which does not use any of a halogen-containing raw material and a halogen-containing catalyst.

On the other hand, a method has been put to practical use, in which carbon dioxide is reacted with ethylene oxide or the like to obtain a cyclic carbonic ester, and the obtained cyclic carbonic ester is reacted with methanol, thereby producing dimethyl carbonate. This method is advantageous in that carbon dioxide as a raw material is harmless, and a corrosive substance, such as hydrochloric acid, is substantially neither used nor generated. However, this method poses the following problems. Ethylene glycol is by-produced in this method; therefore, from the viewpoint of cost reduction, it is necessary to find ways to effectively utilize the by-produced ethylene glycol. Further, it is difficult to perform safe transportation of ethylene (which is a raw material for producing ethylene oxide) and ethylene oxide. Therefore, for obviating the need for the transportation, it is necessary that a plant for producing a carbonic ester by this method be built at a location which is adjacent to a plant for producing ethylene and ethylene oxide.

There is also known a method in which carbon dioxide used as a carbonyl source is subjected to an equilibrium reaction with an alcohol in the presence of a catalyst comprising an organometal compound having a metal-oxygencarbon linkage, thereby forming a carbonic ester and water. This equilibrium reaction is represented by the following formula (3):

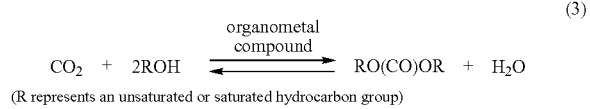

(R represents an unsaturated or saturated hydrocarbon group)

This method is advantageous in that carbon dioxide and an alcohol as raw materials are harmless. However, this method employs an equilibrium reaction in which a carbonic ester and water are simultaneously formed as products. Also in the case of the above-mentioned oxidative carbonylation method using carbon monoxide, water is formed. However, the oxidative carbonylation method does not employ an equilibrium reaction. The equilibrium of an equilibrium reaction using carbon dioxide as a raw material is thermodynamically biased toward the original system. Therefore, the method using the equilibrium reaction has a problem in that, for producing a carbonic ester in high yield, it is necessary that the carbonic ester and water as products be removed from the reaction system. Further, there is also a problem in that the water formed decomposes a catalyst, so that not only is the reaction hindered, but also the number of turnovers of the catalyst (i.e., the number of cycles of regeneration and reuse) is only 2 or 3. For solving this problem, various methods for removing water (which is a product) by using a dehydrating agent have been proposed.

For example, there has been proposed a method in which an alcohol and carbon dioxide are reacted with each other in the presence of a metal alkoxide as a catalyst, thereby forming a carbonic ester and water, wherein a large amount of dicyclohexylcarbodiimide (DCC) (which is an expensive organic dehydrating agent) or the like is used as a dehydrating agent (see Collect. Czech. Chem. Commun. Vol. 60, 687-692 (1995)). This method has a problem in that the dehydrating agent after use cannot be regenerated, resulting in the occurrence of a large amount of a waste derived from the dehydrating agent.

Another method for producing a carbonic ester uses a carboxylic acid orthoester as an organic dehydrating agent (see Unexamined Japanese Patent Application Laid-Open Specification No. Hei 11-35521). (In this patent document, there are descriptions reading: "a carboxylic acid orthoester is reacted with carbon dioxide" and "an acetal is reacted with carbon dioxide". However, as a result of recent studies in the art, it is generally presumed that the actual reaction route is as follows. "An alcohol and carbon dioxide are reacted with each other to obtain a carbonic ester and water. The water is reacted with a carboxylic acid orthoester.") This method has problems in that a carboxylic acid orthoester (which is an expensive compound) is used as a dehydrating agent, and methyl acetate is by-produced (see "Kagaku Sochi (Chemical Equipment)", Vol. 41, No. 2, 52-54 (1999)). Thus, this method is as defective as the above-mentioned methods.

Further, another method uses a large amount of an acetal as an organic dehydrating agent (see German Patent No. 4310109). There is also a patent document in which it is described that an acetal and carbon dioxide are reacted with each other by using, as a catalyst, a metal alkoxide or dibutyltin oxide (see Unexamined Japanese Patent Application Laid-Open Specification No. 2001-31629). (With respect to the reaction described in the latter, as a result of recent studies in the art, it is generally presumed that the actual reaction route is as follows. "An alcohol and carbon dioxide are reacted with each other to obtain a carbonic ester and water. The water is then reacted with an acetal.") However, these patent documents do not teach or suggest a method for efficiently producing an acetal without forming a waste. Further, the methods disclosed in these patent documents have a problem in that, when an acetal is used as a dehydrating agent, large amounts of by-products, such as a ketone and an aldehyde, are formed as wastes.

The effects aimed at by the methods which employ an organic dehydrating agent are to improve the number of turnovers of a catalyst. However, an organic dehydrating agent is consumed in a stoichiometric amount in accordance with the formation of a carbonic ester (and water as a by-product), so that a large amount of an organic dehydrating agent is consumed, thus forming a large amount of a degeneration product of the organic dehydrating agent. Therefore, it is necessary to perform an additional step of regenerating a large amount of a degenerated organic dehydrating agent. Further, in spite of the use of an organic dehydrating agent in a large amount, the possibility still remains that deactivation of a catalyst occurs. The reason is as follows. In the conventional method for producing a carbonic ester by using the equilibrium reaction of the above-mentioned formula (3), carbon dioxide is in a supercritical state. In general, in supercritical carbon dioxide, a catalyst exhibits poor solubility, and the catalyst particles are likely to cohere together.

Therefore, there is a problem in that, when an organotin compound (which is susceptive to polymerization) is used as a catalyst in supercritical carbon dioxide, the organotin compound as a catalyst is likely to be deactivated due to its polymerization.

There has also been proposed a method which employs a solid dehydrating agent (see Applied Catalysis Vol. 142, L1-L3 (1996)). However, this method has a problem in that the solid dehydrating agent cannot be regenerated, thus forming a large amount of a waste.

There is also known a method in which an alcohol (methanol) and carbon dioxide are reacted with each other in the presence of a metal oxide (dibutyltin oxide) to thereby obtain a reaction mixture, and the obtained reaction mixture is cooled and introduced into a packed column containing a solid dehydrating agent, thereby gradually displacing the equilibrium toward a carbonic ester while effecting dehydration, to obtain a carbonic ester (see Unexamined Japanese Patent Application Laid-Open Specification No. 2001-247519). This method is based on a technique in which a conventional technique of using a dehydrating agent is combined with the known phenomenon that the water adsorbability of a conventional dehydrating agent (such as molecular sieves) exhibits a temperature dependency. A dehydrating agent (such as molecular sieves) exhibits lower water adsorbability at high temperatures than at low temperatures. Therefore, for removing a trace amount of water (by-product) from a reaction mixture which contains a largely excess amount of a low molecular weight alcohol used as a solvent, it is necessary to cool the reaction mixture in which an equilibrium is achieved under high temperature and pressure conditions, before introducing the reaction mixture into a packed column containing a solid dehydrating agent. In addition, for increasing the conversion of an alcohol as a raw material, it is necessary that the reaction mixture which has been cooled and dehydrated in the packed column be returned to high temperature and pressure conditions which are necessary for the reaction. Thus, this method has problems in that it is necessary to consume an extremely large amount of energy for cooling and heating, and a large amount of a solid dehydrating agent is needed. This method is very widely used for producing an aliphatic ester having a relatively large equilibrium constant. However, in the production of a carbonic ester from carbon dioxide and an alcohol, wherein the equilibrium of the reaction is largely biased toward the original system, this method cannot be suitably used because this method poses a serious problem that it is necessary to repeat the above-mentioned operation which needs a very large consumption of energy for cooling and heating. Further, for regenerating a degenerated dehydrating agent which has adsorbed water to saturation, it is generally necessary to calcine the degenerated dehydrating agent at several hundreds ° C., thus rendering this method commercially disadvantageous. Furthermore, in this method, only one (water) of the two products of an equilibrium reaction is removed and, therefore, there is a problem in that, when the equilibrium reaction progresses to increase the carbonic ester concentration of the reaction system, the reaction becomes unlikely to progress any more, that is, this method is still under the restriction of an equilibrium reaction. In addition, dibutyltin oxide, which is used as a catalyst in this method, exhibits an extremely poor solubility in methanol and, hence, almost all of dibutyltin oxide as a catalyst remains in solid form in the reaction mixture. Therefore, when the reaction mixture is cooled to room temperature in a cooling step, the reaction mixture turns into a white slurry, thus causing a problem in that, in a subsequent dehydration step performed using a packed column containing a dehydrating agent, the slurry causes clogging of the packed column.

In general, a dehydration method in which water is removed by distillation is well-known in the field of organic synthesis reactions. However, in the field of the production of a carbonic ester from carbon dioxide and an alcohol, although "Study Report of Asahi Glass Association for Promotion of Industrial Technology (Asahi Garasu Kogyogijutsu Shoreikai Kenkyu Hokoku)", Vol. 33, 31-45 (1978) states that "dehydration by distillation is now being studied", there have been no reports or the like which state that a dehydration method using distillation has been completed.

There has been a report which mentions a distillation separation of a carbonic ester from a reaction mixture containing a metal alkoxide, wherein the reaction mixture is obtained by reacting carbon dioxide and an alcohol with each other in the presence of a metal alkoxide catalyst; however, it is known in the art that, when a metal alkoxide catalyst is used, a distillation separation causes a reverse reaction, thus rendering it difficult to recover a carbonic ester by distillation separation (see "Journal of the Chemical Society of Japan (Nippon Kagaku Kaishi)", No. 10, 1789-1794 (1975)). Especially, no method is known by which a carbonic ester having a high boiling point can be separated in high yield from a reaction mixture containing a metal alkoxide.

On the other hand, a metal alkoxide is so unstable that it is susceptive to deactivation due to the moisture in the air. Therefore, in the above-mentioned method, the handling of a metal alkoxide needs strict care. For this reason, no conventional technique using a metal alkoxide catalyst has been employed in the commercial production of a carbonic ester. A metal alkoxide catalyst is an expensive compound, and no technique is known for regenerating a deactivated metal alkoxide catalyst.

There has been proposed a method for producing a carbonic ester by using a dibutyltin dialkoxide as a catalyst, in which, during the reaction, the catalyst is formed from dibutyltin oxide (which is stable to moisture) added to the reaction system (see Japanese Patent No. 3128576). This method has a problem in that, although dibutyltin oxide which is charged into the reaction system is stable, the dibutyltin oxide is converted, during the reaction, into a dibutyltin dialkoxide, which is unstable. Therefore, this method cannot solve the above-mentioned problem of the instability of a metal alkoxide catalyst. Specifically, this method has a defect in that, once the reaction mixture is removed from the reaction system for isolating the carbonic ester obtained as a reaction product, the unstable dibutyltin dialkoxide is deactivated and cannot be regenerated by a conventional technique. Therefore, in this method, there is no other choice but to discard the dibutyltin dialkoxide catalyst (which is expensive) as a waste after the reaction.

On the other hand, it is known that when a metal alkoxide (e.g., a dialkyltin dialkoxide) is heated to about 180° C., the metal alkoxide suffers thermal deterioration form a trialkyltin alkoxide and the like (see "Kougyoukagakuzasshi (Journal of the Society of Chemical Industry)", Vol. 72, No. 7, pages 1543 to 1549 (1969)). It is also known that the trialkyltin alkoxide formed by the thermal deterioration has a very low capability of forming a carbonic ester (see "J. Org. Chem.", Vol. 64, pages 4506 to 4508 (1999)). It is difficult (or substantially impossible) to regenerate a dialkyltin dialkoxide having excellent activity from the trialkyltin alkoxide. Further, the formation of such degraded compound (i.e., an unregenerable unreactive compound) poses a problem in that, when a metal alkoxide is reused as a catalyst, the content of an active catalyst in the metal alkoxide is decreased and, hence, the reaction rate and the yield of a carbonic ester are decreased, rendering a stable production of a carbonic ester difficult. In such cases, for stabilizing the reaction rate and the yield of the carbonic ester, a conventional method in which a small amount of a fresh metal alkoxide is added to the reaction system is employed. However, this method poses a problem in that, when the addition of a fresh metal alkoxide is performed while leaving the deterioration product formed during the reaction as it is in the reaction system, the deterioration product, which has a low catalyst activity, accumulates in a large amount in the reaction system. As apparent also from the above, there is no conventional method in which a metal alkoxide is effectively reused as a catalyst; in any of the conventional methods for producing a carbonic ester, there is no other choice but to discard the metal alkoxide as a waste after the reaction, thus rendering the production of a carbonic ester disadvantageously costly.

Thus, in the conventional methods for producing a carbonic ester by using a metal alkoxide, carbon dioxide and an alcohol, when the metal alkoxide (which is expensive) has lost its catalyst activity due to hydrolysis or the like, there is no way to easily and effectively regenerate and reuse the metal alkoxide. Therefore, the conventional methods for producing a carbonic ester is disadvantageous in that it is necessary to use a large amount of an organic dehydrating agent or a solid dehydrating agent in combination with a small amount of a metal alkoxide.

As described hereinabove, the prior art techniques for producing a carbonic ester have many problems and, therefore, have not been put to practical use.

For solving these problems accompanying the prior art, the present inventors have proposed in WO03/055840 a novel method for producing a carbonic ester. The essential feature of the novel method resides in that the method uses a reaction route in which an organometal compound having a metal-oxygen-carbon linkage is used in a large amount as a precursor of a carbonic ester but not as a catalyst, and the organometal compound is subjected to an addition reaction with carbon dioxide to form an adduct, followed by a thermal decomposition reaction of the adduct, to thereby obtain a reaction mixture containing a carbonic ester. The present inventors have found that a carbonic ester can be produced in high yield by the method. Most of the above-mentioned problems of the prior art have been solved by the method. However, even this method still poses a problem in that an unregenerable unreactive organometal compound is formed during the reaction and accumulates in the reaction system.

SUMMARY OF THE INVENTION

In this situation, the present inventors have made further extensive and intensive studies for solving the above-mentioned problems. In their studies, the present inventors have utilized the techniques of their previous invention disclosed in WO03/055840. As a result, it has unexpectedly been found that the problems can be solved by a method for producing a carbonic ester, comprising the steps of: (1) performing a reaction between a first organometal compound mixture and carbon dioxide, wherein the first organometal compound mixture comprises a mixture of a reactive organometal compound having in its molecule at least two metal-oxygen-carbon linkages and an unregenerable unreactive compound which is derived from the reactive organometal compound, to thereby obtain a reaction mixture containing a carbonic ester formed by the reaction, the unregenerable unreactive compound, and a regenerable metamorphic organometal compound derived from the reactive organometal compound, (2) separating the reaction mixture into a first portion containing the carbonic ester and the unregenerable unreactive compound, and a second portion containing the regenerable metamorphic organometal compound, and (3) reacting the second portion of the reaction mixture with an alcohol to form a second organometal compound mixture and water and removing the water from the second organometal compound mixture, wherein the second organometal compound mixture comprises a mixture of a reactive organometal compound having in its molecule at least two metal-oxygen-carbon linkages and an unregenerable unreactive compound which is derived from the reactive organometal compound. The carbonic ester can be easily isolated from the first portion of the reaction mixture by a conventional method, such as distillation. The second organometal compound mixture obtained in step (3) can be recovered and recycled to step (1), wherein the second organometal compound mixture is used in the above-mentioned reaction for producing a carbonic ester. Based on these findings, the present invention has been completed.

Accordingly, a primary object of the present invention is to provide a method in which a reactive organometal compound used in the reaction can be reused without the need for a large amount of a dehydrating agent and by which commercial production of a carbonic ester in high yield can be performed continuously and repeatedly any number of times while removing an unregenerable unreactive organometal compound from the reaction system.

The foregoing and other objects, features and advantages of the present invention will be apparent from the following detailed description taken in connection with the accompanying drawings and the appended claims.

DETAILED DESCRIPTION OF THE INVENTION

Figure 1:
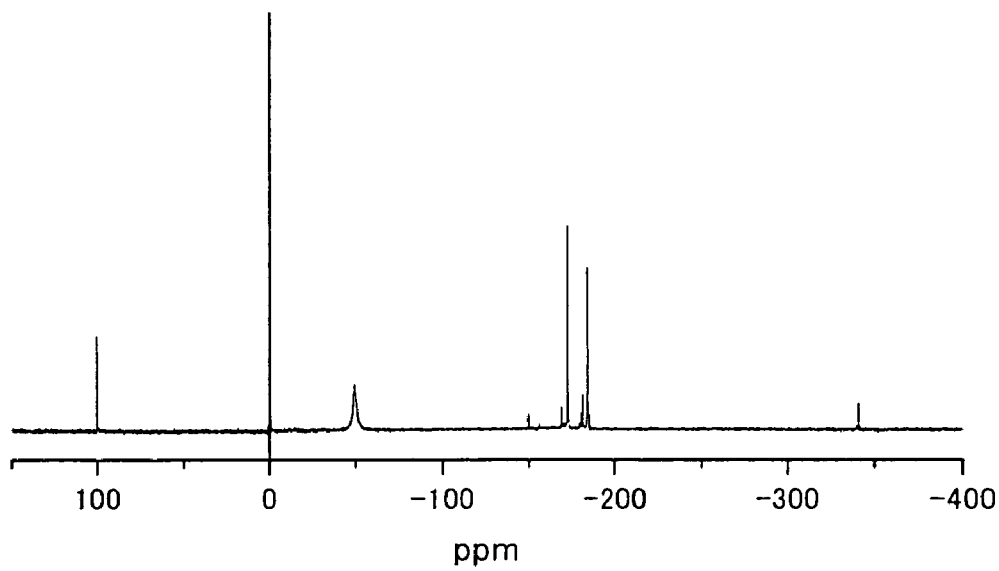
FIG. 1 is the $^{119}$Sn-NMR chart of the reactive organometal compound having a 2-ethylhexyloxy group used in step (1) in Example 1.
Figure 2:
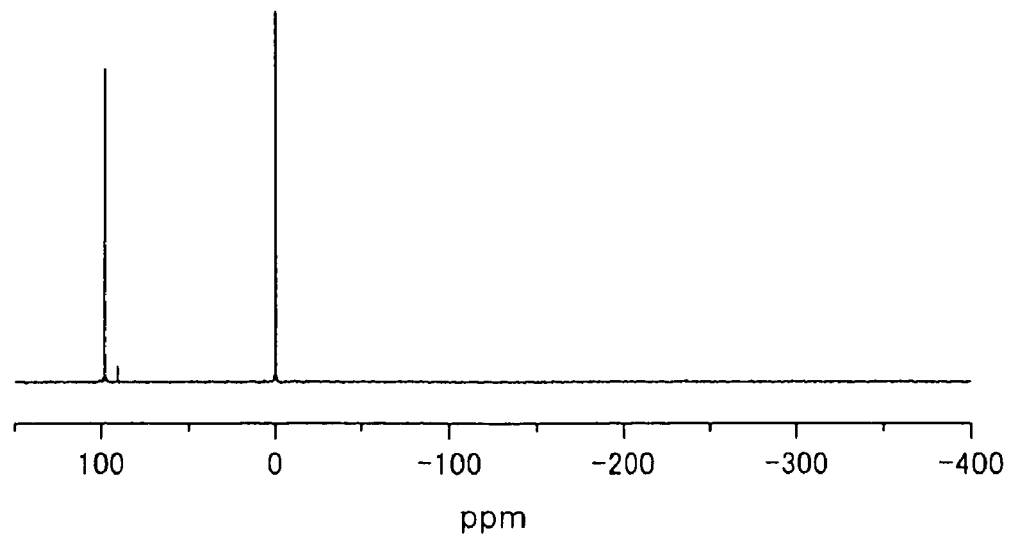
FIG. 2 is the $^{119}$Sn-NMR chart of the unregenerable unreactive compound which is distilled off in step (2) in Example 1.

In the present invention, there is provided a method for producing a carbonic ester, comprising the steps of:

(1) performing a reaction between a first organometal compound mixture and carbon dioxide, the first organometal compound mixture comprising a mixture of a reactive organometal compound having in its molecule at least two metal-oxygen-carbon linkages and an unregenerable unreactive compound which is derived from the reactive organometal compound and which has in its molecule at least three metal-carbon linkages, to thereby obtain a reaction mixture containing a carbonic ester formed by the reaction, the unregenerable unreactive compound, and a regenerable metamorphic organometal compound derived from the reactive organometal compound, (2) separating the reaction mixture into a first portion containing the carbonic ester and the unregenerable unreactive compound, and a second portion containing the regenerable metamorphic organometal compound, and (3) reacting the second portion of the reaction mixture with a first alcohol to form a second organometal compound mixture and water and removing the water from the second organometal compound mixture, the second organometal compound mixture comprising a mixture of a reactive organometal compound having in its molecule at least two metal-oxygen-carbon linkages and an unregenerable unreactive compound which is derived from the reactive organometal compound and which has in its molecule at least three metal-carbon linkages.

For easy understanding of the present invention, the essential features and various preferred embodiments of the present invention are enumerated below.

1. A method for producing a carbonic ester, comprising the steps of:

(1) performing a reaction between a first organometal compound mixture and carbon dioxide, the first organometal compound mixture comprising a mixture of a reactive organometal compound having in its molecule at least two metal-oxygen-carbon linkages and an unregenerable unreactive compound which is derived from the reactive organometal compound and which has in its molecule at least three metal-carbon linkages, to thereby obtain a reaction mixture containing a carbonic ester formed by the reaction, the unregenerable unreactive compound, and a regenerable metamorphic organometal compound derived from the reactive organometal compound, (2) separating the reaction mixture into a first portion containing the carbonic ester and the unregenerable unreactive compound, and a second portion containing the regenerable metamorphic organometal compound, and (3) reacting the second portion of the reaction mixture with a first alcohol to form a second organometal compound mixture and water and removing the water from the second organometal compound mixture, the second organometal compound mixture comprising a mixture of a reactive organometal compound having in its molecule at least two metal-oxygen-carbon linkages and an unregenerable unreactive compound which is derived from the reactive organometal compound and which has in its molecule at least three metal-carbon linkages.

2. The method according to item 1 above, which further comprises, after step (3), a step (4) in which the second organometal compound mixture obtained in step (3) is recovered and recycled to step (1).

3. The method according to item 1 or 2 above, wherein the reactive organometal compound used in step (1) comprises at least one compound selected from the group consisting of:

an organometal compound represented by the formula (1):

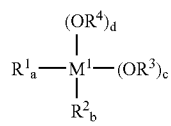

(1)

wherein:
$M^1$ represents a metal atom selected from the group consisting of elements belonging to Groups 4 and 14 of the Periodic Table, exclusive of silicon;

each of $R^1$ and $R^2$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of $R^3$ and $R^4$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of a and b is an integer of from 0 to 2, a+b=0 to 2, each of c and d is an integer of from 0 to 4, and a+b+c+d=4; and an organometal compound represented by the formula (2):

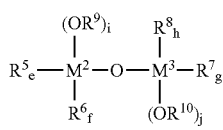

(2)

wherein:
each of $M^2$ and $M^3$ independently represents a metal atom selected from the group consisting of elements belonging to Groups 4 and 14 of the Periodic Table, exclusive of silicon;

each of $R^5$, $R^6$, $R^7$ and $R^8$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of $R^9$ and $R^{10}$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of e, f, g and h is an integer of from 0 to 2, e+f=0 to 2, g+h=0 to 2, each of i and j is an integer of from 1 to 3, e+f+i=3, and g+h+j=3.

4. The method according to item 3 above, wherein each of $R^3$ and $R^4$ in formula (1) and $R^9$ and $R^{10}$ in formula (2) independently represents an n-butyl group, an isobutyl group, a straight chain or branched $C_5$-$C_{12}$ alkyl group, or a straight chain or branched $C_4$-$C_{12}$ alkenyl group.

5. The method according to item 3 above, wherein each of $M^1$ in formula (1) and $M^2$ and $M^3$ in formula (2) represents a tin atom.

6. The method according to item 3 above, wherein the reactive organometal compound used in step (1) is produced from an organotin oxide and an alcohol.

7. The method according to item 1 or 2 above, wherein, in step (1), the reactive organometal compound is used in at least one form selected from the group consisting of a monomeric form, an oligomeric form, a polymeric form and an associated form.

8. The method according to item 1 or 2 above, wherein, in step (1), the reactive organometal compound is used in an amount which is 1/50 to 1 time the stoichiometric amount relative to the amount of the carbon dioxide.

9. The method according to item 1 or 2 above, wherein the reaction in step (1) is performed at 20° C. or higher.

10. The method according to item 1 or 2 above, wherein the reaction in step (1) is performed in the presence of a second alcohol which is the same as or different from the first alcohol used in step (3).

11. The method according to item 1 or 2 above, wherein, in step (2), the separation of the reaction mixture into the first portion and the second portion is performed by at least one separation method selected from the group consisting of distillation, extraction and filtration.

12. The method according to item 1 or 2 above, wherein, in step (2), the separation of the reaction mixture into the first portion and the second portion is performed in the presence of an alcohol which is the same as or different from the first alcohol used in step (3).

13. The method according to item 1 or 2 above, wherein the first alcohol used in step (3) is at least one alcohol selected from the group consisting of an alkyl alcohol having a straight chain or branched $C_1$-$C_{12}$ alkyl group, a cycloalkyl alcohol having a $C_5$-$C_{12}$ cycloalkyl group, an alkenyl alcohol having a straight chain or branched $C_2$-$C_{12}$ alkenyl group, and an aralkyl alcohol having a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl.

14. The method according to item 13 above, wherein the first alcohol has a boiling point which is higher than the boiling point of water, as measured under atmospheric pressure.

15. The method according to item 14 above, wherein the first alcohol is at least one alcohol selected from the group consisting of 1-butanol, 2-methyl-1-propanol, an alkyl alcohol having a straight chain or branched $C_5$-$C_{12}$ alkyl group, an alkenyl alcohol having a straight chain or branched $C_4$-$C_{12}$ alkenyl group, a cycloalkyl alcohol having a $C_5$-$C_{12}$ cycloalkyl group, and an aralkyl alcohol having a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl.

16. The method according to item 1 or 2 above, wherein the removal of the water in step (3) is performed by membrane separation.
17. The method according to item 16 above, wherein the membrane separation is pervaporation.
18. The method according to item 1 or 2 above, wherein the removal of the water in step (3) is performed by distillation.

Hereinbelow, the present invention is described in detail.

As described above, the conventional methods (exclusive of the method proposed by the present inventors in the above-mentioned WO03/055840) for producing a carbonic ester employs an equilibrium reaction represented by the following formula (3):

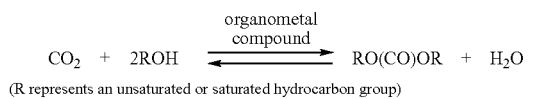

(R represents an unsaturated or saturated hydrocarbon group)

That is, as the conventional methods (exclusive of the method proposed by the present inventors in the above-mentioned WO03/055840), there can be mentioned a method in which a dehydrating agent is used for a reaction mixture containing the equilibrium reaction system (represented by the formula (3) above), wherein the equilibrium reaction system contains a product system comprising a carbonic ester and water; and a method in which a reaction mixture containing the above-mentioned equilibrium reaction system is cooled and subjected to a dehydration treatment in which the reaction mixture is introduced into a packed column containing a solid dehydrating agent, and circulated through the packed column, so as to gradually dehydrate the equilibrium reaction system to thereby suppress a decomposition reaction of the catalyst and accumulate a carbonic ester being formed in a trace amount.

On the other hand, the technical concept of the method of the present invention is completely different from the technical concept of the conventional methods.

The reaction performed in the method of the present invention is basically the same as the reaction performed in the method proposed by the present inventors in the above-mentioned WO03/055840. Before explaining the method of the present invention, the essence of the method of the above-mentioned WO03/055840 is briefly explained below.

The method of WO03/055840 is characterized in:

that a reaction route is used in which an organometal compound having a metal-oxygen-carbon linkage is used in a large amount as a precursor of a carbonic ester but not as a catalyst, and the organometal compound is subjected to an addition reaction with carbon dioxide to form an adduct, followed by a thermal decomposition reaction of the adduct, to thereby obtain a reaction mixture containing a carbonic ester (step (1)), that step (1) is followed by an operation in which the carbonic ester is separated from the reaction mixture to obtain a residual liquid (step (2)), and that step (2) is followed by a reaction of the residual liquid with an alcohol to thereby obtain a reaction mixture comprising an organometal compound having a metal-oxygen-carbon linkage and water, followed by removal of the water from the reaction mixture by distillation or the like, to thereby obtain the organometal compound, whereupon the obtained organometal compound is recovered (step (3)), followed by recycling the organometal compound to step (1) for producing a carbonic ester.

The reactions in step (1) and step (3) of the method of WO03/055840 are represented by the below-mentioned formulae (4) and (5), respectively.

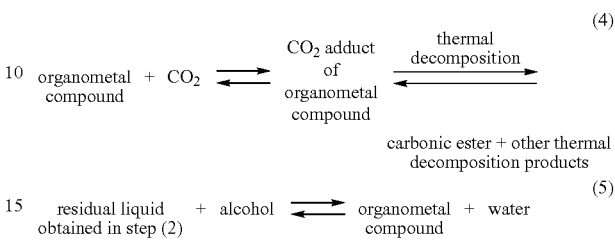

Thus, the method of WO03/055840 is a method in which an organometal compound having a metal-oxygen-carbon linkage is used mainly as a precursor of a carbonic ester, and the organometal compound is subjected to an addition reaction with carbon dioxide to form an adduct, followed by a thermal decomposition reaction of the adduct, to thereby obtain a reaction mixture containing a carbonic ester, whereupon the carbonic ester is separated from the reaction mixture to obtain a residual liquid (containing a thermal decomposition product of the adduct formed by the addition reaction of the organometal compound having a metal-oxygen-carbon linkage with carbon dioxide), followed by an operation in which the residual liquid is reacted with an alcohol to thereby regenerate an organometal compound having a metal-oxygen-carbon linkage. The regenerated organometal compound is recovered and recycled to the step of producing a carbonic ester, and the cycle of these steps is repeated so as to obtain a carbonic ester in a desired amount.

In step (1) of the method of WO03/055840, at least a part of the organometal compound having a metal-oxygen-carbon linkage is converted into a thermal decomposition product thereof and, hence, the reaction mixture obtained in step (1) of the method of WO03/055840 may or may not contain a residual part of the organometal compound having a metal-oxygen-carbon linkage used in step (1). Also, after completion of step (2) of the method of WO03/055840, at least a part of the organometal compound having a metal-oxygen-carbon linkage is converted into a thermal decomposition product or hydrolysis product thereof and, hence, the residual liquid obtained in step (2) of the method of WO03/055840 may or may not contain a residual part of the organometal compound having a metal-oxygen-carbon linkage used in step (1). Anyway, an organometal compound having a metal-oxygen-carbon linkage is regenerated (resynthesized) before completion of step (3) of the method of WO03/055840.

In the conventional methods using the equilibrium reaction of the formula (3) above, the entire reaction is held under equilibrium. By contrast, in the method of the previous invention, the equilibrium reaction of the formula (3) above can be effectively divided into consecutive reactions which can be easily controlled, thereby rendering it possible to efficiently produce a carbonic ester while separating the carbonic ester and water from the reaction system. Specifically, in step (1) of the method of WO03/055840, a reaction can be performed in the absence of water. In step (2) of the method of WO03/055840, a reverse reaction of a carbonic ester and other thermal decomposition products can be prevented by separating a carbonic ester from the reaction mixture. In step (3) of the method of WO03/055840, after the regeneration of an organometal compound having a metal-oxygen-carbon linkage, the organometal compound can be recovered by removing water. Further, in each step of the method of WO03/055840, the operation conditions can be easily optimized by appropriately employing conventional techniques of chemical synthesis, such as cooling, heating, stirring, pressurizing, decompression and separation.

As mentioned above, the method of the present invention has been completed as a result of the extensive and intensive studies for improving the above-mentioned method proposed by the present inventors in WO03/055840. The method of WO03/055840 poses a problem in that an unregenerable unreactive organometal compound (i.e., a degraded compound) formed in the reaction gradually accumulates in the reaction system. However, this problem can be easily solved by the method of the present invention. Generally, an organometal compound is susceptive to thermal deterioration. Therefore, when an organometal compound which has been used is recycled, the reaction system contains a mixture of an active organometal compound and an organometal compound having an extremely low activity (i.e., unregenerable unreactive organometal compound, which is a degraded compound), wherein the ratio of the unregenerable unreactive organometal compound to the active organometal compound gradually becomes large. Therefore, for a stable production of a carbonic ester, it is necessary to continuously feed a fresh, active organometal compound or a raw material thereof during the reaction. In the field of the production of a carbonic ester from carbon dioxide and an alcohol, it is difficult to separate a degraded compound (derived from the organometal compound) formed during the reaction. Although some prior art documents concerning such method describe the recycle of the organometal compound, there has been no conventional technique for removing the degraded compound (derived from the organometal compound) from the reaction system. On the other hand, in the field of the production of a carbonic ester in the presence of a conventional catalyst, a method has been practiced in which a part of the catalyst having been used for the reaction for producing a carbonic ester is taken out from the reaction system and a fresh catalyst is fed in an amount which corresponds to the amount of the catalyst having lost its catalyst activity. However, this method poses a problem in that, for taking out the deactivated catalyst, it is necessary to take out a part of the active catalyst in an amount which is several times or dozens of times the amount of the deactivated catalyst. Therefore, when a reaction is performed by using this method in the presence of an expensive catalyst, the production cost becomes very high. Thus, it is virtually impossible to practice this method on a commercial scale. Accordingly, in this conventional method, when a catalyst is recycled, it is important to selectively remove the degraded compound from the reaction system. As a result of their extensive and intensive studies, the present inventors have found that the degraded compound has physical properties (such as the boiling point and the physical state, e.g., the solid form or the liquid form) and chemical properties (such as hydrolyzability) which are different from those of the useful organometal compounds (i.e., a reactive organometal compound and a regenerable metamorphic organometal compound). Based on this finding, the present inventors have completed the present invention, which is directed to a method in which an organometal compound can be repeatedly used while selectively withdrawing at least a part of a degraded compound derived from the reactive organometal compound.

The method of the present invention is a method for producing a carbonic ester, comprising the step of:

(1) performing a reaction between a first organometal compound mixture and carbon dioxide, the first organometal compound mixture comprising a mixture of a reactive organometal compound having in its molecule at least two metal-oxygen-carbon linkages and an unregenerable unreactive compound which is derived from the reactive organometal compound and which has in its molecule at least three metal-carbon linkages, to thereby obtain a reaction mixture containing a carbonic ester formed by the reaction, the unregenerable unreactive compound, and a regenerable metamorphic organometal compound derived from the reactive organometal compound, (2) separating the reaction mixture into a first portion containing the carbonic ester and the unregenerable unreactive compound, and a second portion containing the regenerable metamorphic organometal compound, and (3) reacting the second portion of the reaction mixture with a first alcohol to form a second organometal compound mixture and water and removing the water from the second organometal compound mixture, the second organometal compound mixture comprising a mixture of a reactive organometal compound having in its molecule at least two metal-oxygen-carbon linkages and an unregenerable unreactive compound which is derived from the reactive organometal compound and which has in its molecule at least three metal-carbon linkage hereinbelow, an explanation is given with respect to the compounds used in the method of the present invention.

In step (1) of the method of the present invention, a reactive organometal compound having a metal-oxygen-carbon linkage is used. The reactive organometal compound used in step (1) of the method of the present invention has in its molecule at least two metal-oxygen-carbon linkages. As an example of such organometal compound, there can be mentioned a reactive organometal compound having at least two alkoxy groups. It is preferred that the reactive organometal compound used in step (1) comprises at least one compound selected from the group consisting of:

an organometal compound represented by the formula (1):

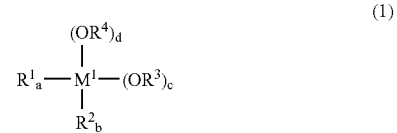

wherein:
M$^1$ represents a metal atom selected from the group consisting of elements belonging to Groups 4 and 14 of the Periodic Table, exclusive of silicon;
each of R$^1$ and R$^2$ independently represents a straight chain or branched C$_1$-C$_{12}$ alkyl group, a C$_5$-C$_{12}$ cycloalkyl group, a straight chain or branched C$_2$-C$_{12}$ alkenyl group, a C$_7$-C$_{20}$ aralkyl group comprised of unsubstituted or substituted C$_6$-C$_{19}$ aryl and alkyl selected from the group consisting of straight chain or branched C$_1$-C$_{14}$ alkyl and C$_5$-C$_{14}$ cycloalkyl, or an unsubstituted or substituted C$_6$-C$_{20}$ aryl group;
each of R$^3$ and R$^4$ independently represents a straight chain or branched C$_1$-C$_{12}$ alkyl group, a C$_5$-C$_{12}$ cycloalkyl group, a straight chain or branched C$_2$-C$_{12}$ alkenyl group, or a C$_7$-C$_{20}$ aralkyl group comprised of unsubstituted or substituted C$_6$-C$_{19}$ aryl and alkyl selected from the group consisting of straight chain or branched $C_1$-$C_{14}$ alkyl and $C_5$-$C_{14}$ cycloalkyl; and each of a and b is an integer of from 0 to 2, a+b=0 to 2, each of c and d is an integer of from 0 to 4, and a+b+c+d=4; and an organometal compound represented by the formula (2):

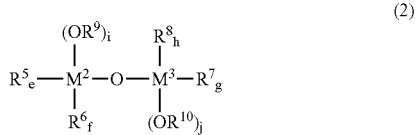

wherein:
each of $M^2$ and $M^3$ independently represents a metal atom selected from the group consisting of elements belonging to Groups 4 and 14 of the Periodic Table, exclusive of silicon;

each of $R^5$, $R^6$, $R^7$ and $R^8$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

each of $R^9$ and $R^{10}$ independently represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of e, f, g and h is an integer of from 0 to 2, e+f=0 to 2, g+h=0 to 2, each of i and j is an integer of from 1 to 3, e+f+i=3, and g+h+j=3.

The Periodic Table mentioned herein is as prescribed in the IUPAC (International Union of Pure and Applied Chemistry) nomenclature system (1989).

In the method of the present invention, the above-mentioned organometal compound is used in at least one form selected from the group consisting of a monomeric form, an oligomeric form, a polymeric form and an associated form.

Each of $M^1$ in the organometal compound represented by formula (1) above and $M^2$ and $M^3$ in the organometal compound represented by formula (2) above independently represents a metal atom selected from the group consisting of elements belonging to Groups 4 and 14 of the Periodic Table, exclusive of silicon. It is preferred that each of $M^1$, $M^2$ and $M^3$ is a metal atom selected from the group consisting of a titanium atom, a tin atom and a zirconium atom. From the viewpoint of the solubility in and reactivity with an alcohol, it is more preferred that each of $M^1$, $M^2$ and $M^3$ is a tin atom.

Examples of $R^1$ and $R^2$ in the organometal compound represented by formula (1) above and $R^5$, $R^6$, $R^7$ and $R^8$ in the organometal compound represented by formula (2) above include $C_1$-$C_{12}$ alkyl groups (which are aliphatic hydrocarbon groups) and $C_5$-$C_{12}$ cycloalkyl groups (which are alicyclic hydrocarbon groups), such as a methyl group, an ethyl group, a propyl group, an n-butyl group (and isomers thereof), a butyl group (and isomers thereof), a pentyl group (and isomers thereof), a hexyl group (and isomers thereof), a heptyl group (and isomers thereof), an octyl group (and isomers thereof), a nonyl group (and isomers thereof), a decyl group (and isomers thereof), an undecyl group (and isomers thereof), a dodecyl group (and isomers thereof), a 2-butenyl group, a cyclobutenyl group, a cyclobutyl group, a cyclopentyl group, a cyclohexyl group, a cyclopentadienyl group and a cyclohexenyl group; $C_7$-$C_{20}$ aralkyl groups, such as a benzyl group and a phenylethyl group; and $C_6$-$C_{20}$ aryl groups, such as a phenyl group, a tolyl group and a naphthyl group. Each of these hydrocarbon groups may have an ether linkage. Moreover, each of these hydrocarbon groups may be a halogenated hydrocarbon group (i.e., hydrocarbon group which has at least one hydrogen atom thereof replaced by a halogen atom), such as a nonafluorobutyl group or a heptafluorobutyl group (and isomers thereof). However, $R^1$, $R^2$, $R^5$, $R^6R^7$ and $R^8$ are not limited to these examples. Of the above-mentioned groups, lower alkyl groups are preferred, and straight chain or branched $C_1$-$C_4$ alkyl groups are more preferred. Hydrocarbon groups having more carbon atoms than mentioned above can also be used as $R^1$, $R^2$, $R^5$, $R^6$, $R^7$ and $R^8$; however, when such groups having a larger number of carbon atoms are used, there is a danger that the fluidity of the organometal compound and/or the productivity of a carbonic ester becomes low. Examples of $R^3$ and $R^4$ in the organometal compound represented by formula (1) above and $R^9$ and $R^{10}$ in the organometal compound represented by formula (2) above include $C_1$-$C_{12}$ alkyl groups (which are aliphatic hydrocarbon groups) and $C_5$-$C_{12}$ cycloalkyl groups (which are alicyclic hydrocarbon groups), such as a methyl group, an ethyl group, a propyl group (and isomers thereof), a butyl group (and isomers thereof), a 2-butenyl group, a pentyl group (and isomers thereof), a hexyl group (and isomers thereof), an octyl group (and isomers thereof), a nonyl group (and isomers thereof), a decyl group (and isomers thereof), an undecyl group (and isomers thereof), a dodecyl group (and isomers thereof), a cyclopropyl group, a cyclobutyl group, a cyclopentyl group, a cyclopentadienyl group, a cyclohexyl group, a cyclohexenyl group, a methoxyethyl group, an ethoxymethyl group and an ethoxyethyl group; and $C_7$-$C_{20}$ aralkyl groups, such as a benzyl group and a phenylethyl group. However, $R^3$, $R^4$, $R^9$ and $R^{10}$ are not limited to these examples. Of the above-mentioned groups, preferred are organometal compounds in which each of the corresponding alcohols (i.e., $R^3OH$, $R^4OH$, $R^9OH$ and $R^{10}OH$) has a boiling point higher than that of water (wherein the boiling point is measured under atmospheric pressure). Further, from the viewpoint of recycling the organometal compound regenerated in step (3), it is most preferred that, in the organometal compound represented by formula (1) and/or formula (2) above, the alkyl or alkenyl moiety of each of the alkoxy group is n-butyl, isobutyl, a straight chain or branched $C_5$-$C_{12}$ alkyl or a straight chain or branched $C_4$-$C_{12}$ alkenyl.

Examples of reactive organometal compounds represented by formula (1) above include alkoxytin compounds, alkoxytitanium compounds and alkylalkoxytin compounds. Specific examples of such organometal compounds include tetramethoxytin, tetraethoxytin, tetrapropyloxytin (and isomers thereof), tetrabutyloxytin (and isomers thereof), tetrapentyloxytin (and isomers thereof), tetrahexyloxytin (and isomers thereof), tetraheptyloxytin (and isomers thereof), tetraoctyloxytin (and isomers thereof), tetranonyloxytin (and isomers thereof), dimethoxydiethoxytin, tetramethoxytitanium, tetraethoxytitanium, tetrapropyloxytitanium, tetraisopropyloxytitanium, tetrakis(2-ethyl-1-hexyloxy)titanium, tetrabenzyloxytin, dimethoxydiethoxytin, diethoxydipropyloxytin (and isomers thereof), dimethoxydihexyloxytin (and isomers thereof), dimethyldimethoxytin, dimethyldiethoxytin, dimethyldipropyloxytin (and isomers thereof), dimethyldibutyloxytin (and isomers thereof), dimethyldipentyloxytin (and isomers thereof), dimethyldihexyloxytin (and isomers thereof), dimethyldiheptyloxytin (and isomers thereof), dimethyldioctyloxytin (and isomers thereof), dimethyldinonyloxytin (and isomers thereof), dimethyldidecyloxytin (and isomers thereof), dibutyltin dimethoxide, dibutyltin diethoxide, dibutyltin dipropoxide (and isomers thereof), dibutyltin dibutoxide (and isomers thereof), dibutyltin dipentyloxide (and isomers thereof), dibutyltin dihexyloxide (and isomers thereof), dibutyltin diheptyloxide (and isomers thereof), dibutyltin dioctyloxide (and isomers thereof), dibutyltin dinonyloxide (and isomers thereof), dibutyltin didecyloxide (and isomers thereof), dibutyltin dibenzyloxide, dibutyltin diphenylethoxide, diphenyltin dimethoxide, diphenyltin diethoxide, diphenyltin dipropoxide (and isomers thereof), diphenyltin dibutoxide (and isomers thereof), diphenyltin dipentyloxide (and isomers thereof), diphenyltin dihexyloxide (and isomers thereof), diphenyltin diheptyloxide (and isomers thereof), diphenyltin dioctyloxide (and isomers thereof), diphenyltin dinonyloxide (and isomers thereof), diphenyltin didecyloxide (and isomers thereof), diphenyltin dibenzyloxide, diphenyltin diphenylethoxide, bis(trifluorobutyl)tin dimethoxide, bis(trifluorobutyl)tin diethoxide, bis(trifluorobutyl)tin dipropoxide (and isomers thereof) and bis(trifluorobutyl)tin dibutoxide (and isomers thereof).

Examples of reactive organometal compounds represented by formula (2) above include alkoxydistannoxanes and aralkyloxydistannoxanes. Specific examples of such organometal compounds include 1,1,3,3-tetramethyl-1,3-dimethoxydistannoxane, 1,1,3,3-tetramethyl-1,3-diethoxydistannoxane, 1,1,3,3-tetramethyl-1,3-dipropyloxydistannoxane (and isomers thereof), 1,1,3,3-tetramethyl-1,3-dibutyloxydistannoxane (and isomers thereof), 1,1,3,3-tetramethyl-1,3-dipentyloxydistannoxane (and isomers thereof), 1,1,3,3-tetramethyl-1,3-dihexyloxydistannoxane (and isomers thereof), 1,1,3,3-tetramethyl-1,3-diheptyloxydistannoxane (and isomers thereof), 1,1,3,3-tetramethyl-1,3-dioctyloxydistannoxane (and isomers thereof), 1,1,3,3-tetramethyl-1,3-dinonyloxydistannoxane (and isomers thereof), 1,1,3,3-tetramethyl-1,3-didecyloxydistannoxane (and isomers thereof), 1,1,3,3-tetramethyl-1,3-dibenzyloxydistannoxane, 1,1,3,3-tetramethyl-1,3-diphenylethoxydistannoxane, 1,1,3,3-tetrabutyl-1,3-dimethoxydistannoxane, 1,1,3,3-tetrabutyl-1,3-diethoxydistannoxane, 1,1,3,3-tetrabutyl-1,3-dipropyloxydistannoxane (and isomers thereof), 1,1,3,3-tetrabutyl-1,3-dibutyloxydistannoxane (and isomers thereof), 1,1,3,3-tetrabutyl-1,3-dipentyloxydistannoxane (and isomers thereof), 1,1,3,3-tetrabutyl-1,3-dihexyloxydistannoxane (and isomers thereof), 1,1,3,3-tetrabutyl-1,3-diheptyloxydistannoxane (and isomers thereof), 1,1,3,3-tetrabutyl-1,3-dioctyloxydistannoxane (and isomers thereof), 1,1,3,3-tetrabutyl-1,3-dinonyloxydistannoxane (and isomers thereof), 1,1,3,3-tetrabutyl-1,3-didecyloxydistannoxane (and isomers thereof), 1,1,3,3-tetrabutyl-1,3-dibenzyloxydistannoxane, 1,1,3,3-tetrabutyl-1,3-diphenylethoxydistannoxane, 1,1,3,3-tetraphenyl-1,3-dimethoxydistannoxane, 1,1,3,3-tetraphenyl-1,3-diethoxydistannoxane, 1,1,3,3-tetraphenyl-1,3-dipropyloxydistannoxane (and isomers thereof), 1,1,3,3-tetraphenyl-1,3-dibutyloxydistannoxane (and isomers thereof), 1,1,3,3-tetraphenyl-1,3-dipentyloxydistannoxane (and isomers thereof), 1,1,3,3-tetraphenyl-1,3-dihexyloxydistannoxane (and isomers thereof), 1,1,3,3-tetraphenyl-1,3-diheptyloxydistannoxane (and isomers thereof), 1,1,3,3-tetraphenyl-1,3-dioctyloxydistannoxane (and isomers thereof), 1,1,3,3-tetraphenyl-1,3-dinonyloxydistannoxane (and isomers thereof), 1,1,3,3-tetraphenyl-1,3-didecyloxydistannoxane (and isomers thereof), 1,1,3,3-tetraphenyl-1,3-dibenzyloxydistannoxane, 1,1,3,3-tetraphenyl-1,3-diphenylethoxydistannoxane, 1,1,3,3-tetrakis(trifluorobutyl)-1,3-dimethoxydistannoxane, 1,1,3,3-tetrakis(trifluorobutyl)-1,3-diethoxydistannoxane, 1,1,3,3-tetrakis(trifluorobutyl)-1,3-dipropyloxydistannoxane (and isomers thereof), 1,1,3,3-tetrakis(trifluorobutyl)-1,3-dibutyloxydistannoxane (and isomers thereof), 1,1,3,3-tetrakis(pentafluorobutyl)-1,3-dimethoxydistannoxane, 1,1,3,3-tetrakis(pentafluorobutyl)-1,3-diethoxydistannoxane, 1,1,3,3-tetrakis(pentafluorobutyl)-1,3-dipropyloxydistannoxane (and isomers thereof), 1,1,3,3-tetrakis(pentafluorobutyl)-1,3-dibutyloxydistannoxane (and isomers thereof), 1,1,3,3-tetrakis(pentafluorobutyl)-1,3-dipentyloxydistannoxane (and isomers thereof), 1,1,3,3-tetrakis(pentafluorobutyl)-1,3-dihexyloxydistannoxane (and isomers thereof), 1,1,3,3-tetrakis(heptafluorobutyl)-1,3-dimethoxydistannoxane, 1,1,3,3-tetrakis(heptafluorobutyl)-1,3-diethoxydistannoxane, 1,1,3,3-tetrakis(heptafluorobutyl)-1,3-dipropyloxydistannoxane (and isomers thereof), 1,1,3,3-tetrakis(heptafluorobutyl)-1,3-dibutyloxydistannoxane (and isomers thereof).

The above-mentioned reactive organometal compounds may be used individually or in combination. Further, orgnometal compounds other than mentioned above or inorganic metal compounds may be used in combination with the above-mentioned reactive organometal compounds. As a reactive organometal compound, those reactive organometal compounds which are commercially available may be used. Alternatively, reactive organometal compounds represented by formula (1) above may be obtained by a conventional method (e.g., a method described in Dutch Patent No. 6612421) in which dibutyltin oxide, an alcohol having 4 or more carbon atoms and a solvent exhibiting an azeotropy with water are mixed together to effect a reaction, and the resultant is subjected to distillation, thereby obtaining a fraction containing a reactive organometal compound represented by formula (1) above. The above-mentioned Dutch Patent No. 6612421 describes that this method cannot be employed for obtaining an organometal compound having a $C_1$-$C_3$ alkoxy group and that an organometal compound having a $C_1$-$C_3$ alkoxy group can be obtained from dibutyltin dichloride and sodium alcoholate. On the other hand, by employing a method described in Japanese Patent Application No. 2001-396537 or Japanese Patent Application No. 2001-396545, there can be obtained an organometal compound represented by formula (1) or (2) from a metal oxide and an alcohol. By this method, there can be obtained an organometal compound having a $C_1$-$C_3$ alkoxy group, such as a methoxy group. For example, an organometal compound having a methoxy group can be obtained from dibutyltin oxide, methanol and hexane. It is known that, in such a case, methanol and hexane form a minimum boiling azeotrope. However, the present inventors have unexpectedly found that, by this method, the removal of water can be performed, even though the methanol/hexane mixture has a boiling point lower than that of water. Based on this finding, the present inventors have developed a method for producing an organometal compound from an alcohol having a boiling point lower than that of water. An organometal compound obtained from dibutyltin oxide and an alcohol having a boiling point lower than that of water tends to be comprised mainly of an organometal compound represented by formula (2). However, when it is desired to obtain a large amount of an organometal compound represented by formula (1), it can be achieved by subjecting the above-mentioned organometal compound comprised mainly of an organometal compound represented by formula (2) to distillation, thereby obtaining a fraction comprising an organometal compound represented by formula (1). Alternatively, an organometal compound represented by formula (1) can be obtained by performing a reaction of dialkyltin dichloride and an alcoholate.

In the present invention, in connection with the above-mentioned reactive organometal compound, the term "regenerable metamorphic organometal compound derived from the reactive organometal compound" and the term "unregenerable unreactive (organometal) compound derived from the reactive organometal compound" are used. With respect to these terms, explanations are given below. The reactive organometal compound used in the present invention is an organometal compound having in its molecule at least two metal-oxygen-carbon linkages. In the present invention, the term "regenerable metamorphic organometal compound derived from the reactive organometal compound" is used to indicate compounds which are comprised mainly of the decomposition products formed by the thermal decomposition of the above-mentioned adduct ($CO_2$ adduct) formed by the reaction of the reactive organometal compound with carbon dioxide, wherein the thermal decomposition products are formed simultaneously with the formation of the carbonic ester. It is difficult to specify the detailed structure of the regenerable metamorphic organometal compound. However, as regenerable metamorphic organometal compounds, there can be also mentioned a hydrolysis product of the reactive organometal compound and a hydrolysis product of the carbon dioxide adduct of the reactive organometal compound.

On the other hand, the term "unregenerable unreactive (organometal) compound derived from the reactive organometal compound" (or simply "degraded compound") is used to indicate compounds which are unregenerable organometal compounds (formed by a thermal degradation of the reactive organometal compound and/or the carbon dioxide adduct thereof) having an extremely low activity. A degraded compound (i.e., unregenerable unreactive compound) is formed mainly in step (3). However, a degraded compound is sometimes formed in a step for producing the reactive organometal compound. As a representative example of the degraded compound, there can be mentioned a compound having, per metal atom in a molecule thereof, at least three metal-carbon linkages. As an example of such a compound, there can be mentioned a compound represented by the following formula (6):

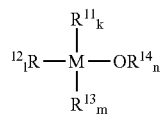

(6)

wherein:
M represents a metal atom selected from the group consisting of elements belonging to Groups 4 and 14 of the Periodic Table, exclusive of silicon;
each of $R^{11}$, $R^{12}$ and $R^{13}$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;
$R^{14}$ represents a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and
each of k, l and m is an integer of from 0 to 4, k+l+m=3 or 4, n is an integer of 0 or 1, and k+l+m+n=4.

Specific examples of degraded compounds of formula (6) above include tetraalkyltin and trialkyltin alkoxide. Further examples of degraded compounds (unreactive compounds) include metal oxides, such as $SnO_2$, $TiO_2$ and $ZrO_2$.

The degraded compound (such as the above-mentioned compound having, per metal atom in a molecule thereof, at least three metal-carbon linkages) has physical and chemical properties different from those of the useful organometal compound (i.e., the reactive organometal compound or the regenerable metamorphic organometal compound). Specifically, the degraded compound is different from the useful organometal compound mainly in that the degraded compound has a boiling point lower than that of the useful organometal compound and is less susceptible to hydrolysis than the useful organometal compound.

Hereinbelow, explanations are given with respect to the alcohols used in the method of the present invention.

In the method of the present invention, a first alcohol is used in step (3). In addition, a second alcohol may be optionally used in step (1). Further, an alcohol may be optionally used in step (2) (hereinafter, this alcohol is frequently referred to as a "third alcohol").

The first, second and third alcohols may be the same or different from one another. Examples of such alcohols include alkyl alcohols having a straight chain or branched $C_1$-$C_{12}$ alkyl group, cycloalkyl alcohols having a $C_5$-$C_{12}$ cycloalkyl group, alkenyl alcohols having a straight chain or branched $C_2$-$C_{12}$ alkenyl group, and aralkyl alcohols having a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl.

Specific examples of these alcohols include $C_1$-$C_{12}$ aliphatic alcohols and $C_5$-$C_{12}$ alicyclic alcohols, such as methanol, ethanol, propanol, 2-propanol, 1-butanol, 2-butanol (and isomers thereof), 2-methyl-1-propanol, 2-methyl-2-propanol, cyclobutanol, 1-pentanol, 2-pentanol (and isomers thereof), 3-pentanol, 3-methyl-1-butanol, 2-methyl-1-butanol, 2-methyl-2-butanol (and isomers thereof), 3-methyl-2-butanol (and isomers thereof), cyclopentanol, 2-methyl-1-cyclobutanol (and isomers thereof), 3-methyl-1-cyclobutanol (and isomers thereof), 1-methyl-1-cyclobutanol (and isomers thereof), cyclobutylmethanol (and isomers thereof), 1-hexanol, 2-hexanol (and isomers thereof), 3-hexanol (and isomers thereof), 4-methyl-1-pentanol (and isomers thereof), 3-methyl-1-pentanol (and isomers thereof), 2-methyl-1-pentanol (and isomers thereof), 2-ethyl-1-butanol, 3-methyl-2-pentanol (and isomers thereof), 3-methyl-3-pentanol (and isomers thereof), cyclohexanol, 1-methyl-1-cyclopentanol (and isomers thereof), 2-methyl-1-cyclopentanol (and isomers thereof), 2-cyclobutylethanol (and isomers thereof), 1-cyclobutylethanol (and isomers thereof), (1-methylcyclobutyl)methanol (and isomers thereof), (2-methylcyclobutyl)methanol (and isomers thereof), heptanol (and isomers thereof), cyclohexylmethanol (and isomers thereof), (methylcyclohexyl)methanol (and isomers thereof), cyclohexylethanol (and isomers thereof), (ethylcyclobutyl)methanol (and isomers thereof), (methylcyclopropyl)ethanol (and isomers thereof), (ethylcyclopropyl)methanol (and isomers thereof), octanol (and isomers thereof), nonanol (and isomers thereof), decanol (and isomers thereof), undecanol (and isomers thereof), dodecanol (and isomers thereof), propenyl alcohol, butenyl alcohol (and isomers thereof), pentenyl alcohol (and isomers thereof), cyclopentenol (and isomers thereof), cyclopentadienyl alcohol, hexenol (and isomers thereof) and cyclohexenol (and isomers thereof); and aralkyl alcohols, such as benzyl alcohol and phenylethyl alcohol.

Further, as the first, second and third alcohols, polyhydric alcohols may be used. Examples of polyhydric alcohols include polyhydric $C_1$-$C_{12}$ aliphatic alcohols and polyhydric $C_5$-$C_{12}$ alicyclic alcohols, such as ethylene glycol, 1,3-propanediol, 1,2-propanediol, cyclohexanediol and cyclopentanediol; and aralkyl alcohols, such as benzenedimethanol.

Among the above-mentioned alcohols, preferred are $C_1$-$C_8$ primary or secondary monohydric alcohols, such as methanol, ethanol, propanol, 2-propanol, 1-butanol, 2-butanol (and isomers thereof), 2-methyl-1-propanol, 2-methyl-2-propanol, cyclobutanol, 1-pentanol, 2-pentanol (and isomers thereof), 3-pentanol, 3-methyl-1-butanol, 2-methyl-1-butanol, 2-methyl-2-butanol (and isomers thereof), 3-methyl-2-butanol (and isomers thereof), cyclopentanol, 2-methyl-1-cyclobutanol (and isomers thereof), 3-methyl-1-cyclobutanol (and isomers thereof), 1-methyl-1-cyclobutanol (and isomers thereof), cyclobutylmethanol (and isomers thereof), 1-hexanol, 2-hexanol (and isomers thereof), 3-hexanol (and isomers thereof), 4-methyl-1-pentanol (and isomers thereof), 3-methyl-1-pentanol (and isomers thereof), 2-methyl-1-pentanol (and isomers thereof), 2-ethyl-1-butanol, 3-methyl-2-pentanol (and isomers thereof), 3-methyl-3-pentanol (and isomers thereof), cyclohexanol, 1-methyl-1-cyclopentanol (and isomers thereof), 2-methyl-1-cyclopentanol (and isomers thereof), 2-cyclobutylethanol (and isomers thereof), 1-cyclobutylethanol (and isomers thereof), (1-methylcyclobutyl)methanol (and isomers thereof), (2-methylcyclobutyl)methanol (and isomers thereof), heptanol (and isomers thereof), cyclohexylmethanol (and isomers thereof), (methylcyclohexyl)methanol (and isomers thereof), cyclohexylethanol (and isomers thereof), (ethylcyclobutyl)methanol (and isomers thereof), (methylcyclopropyl)ethanol (and isomers thereof), (ethylcyclopropyl)methanol (and isomers thereof), octanol (and isomers thereof) and hexenol; and $C_7$-$C_8$ primary or secondary aralkyl alcohols, such as benzyl alcohol.

Among the above-mentioned alcohols, more preferred are the alkyl alcohols, the cycloalkyl alcohols, the alkenyl alcohols and the aralkyl alcohols, which have a boiling point higher than that of water (wherein the boiling point is measured under atmospheric pressure). Examples of such alcohols include 1-butanol, 2-methyl-1-propanol, an alkyl alcohol having a straight chain or branched $C_5$-$C_{12}$ alkyl group, an alkenyl alcohol having a straight chain or branched $C_4$-$C_{12}$ alkenyl group, a cycloalkyl alcohol having a $C_5$-$C_{12}$ cycloalkyl group and an aralkyl alcohol having a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl. Among these alcohols, most preferred are alkyl alcohols having a straight chain or branched $C_5$-$C_8$ alkyl group.

Hereinbelow, explanations are given on the method for analyses of the reactive organometal compound and the degraded compound derived therefrom.

The reactive organometal compounds which are, respectively, represented by formulae (1) and (2), and the degraded compound (the unregenerable unreactive compound) can be analyzed by, for example, the Sn-119 Nuclear Magnetic Resonance (119Sn-NMR) spectroscopy (see, for example, U.S. Pat. No. 5,545,600). However, in a $^{119}$Sn-NMR spectrum, a chemical shift value ascribed to the structure of the organometal compound represented by formula (1) largely varies depending, for example, on the organometal compound content of the sample used for the $^{119}$Sn-NMR analysis and on the presence or absence of an alcohol in the sample used for the $^{119}$Sn-NMR analysis. Therefore, it is preferred that the analysis of the organometal compound is performed by a method in which the proton nuclear magnetic resonance ($^1$H-NMR) spectroscopy and the carbon-13 nuclear magnetic resonance ($^{13}$C-NMR) spectroscopy are used in combination with the 119Sn-NMR spectroscopy. Table 1 below shows $^{119}$Sn-NMR data of examples of chemical shift values ascribed to the structure of a reactive orgnometal compound represented by formula (1), which is produced from 2-ethyl-1-hexanol and dibutyltin oxide. Table 2 below shows $^{119}$Sn-NMR data of examples of chemical shift values ascribed to the structure of a degraded compound (i.e., unregenerable unreactive organometal compound) represented by formula (6). In the $^{119}$Sn-NMR chart of the degraded compound, the chemical shift value ascribed to the structure of the degraded compound does not depend very much on the degraded compound content of the sample used for the $^{119}$Sn-NMR analysis, but mainly on the types of alkyl groups and alkoxy group contained in the degraded compound. The characteristic feature of the $^{119}$Sn-NMR chart of the degraded compound resides in that signals ascribed to the structure of the degraded compound appear in the range of from δ 90 to 110 ppm.

TABLE 1

Contents of an organometal compound of formula (1) having a 2-ethylhexyloxy group in sample solutions, and $^{119}$Sn-NMR chemical shift values obtained with respect to the sample solutions
$^{119}$Sn-NMR data

| Organometal compound content (wt %) | Chemical shift value (δ ppm) |
|---|---|
| 48.0 | −64.2 |
| 20.5 | −19.1 |
| 11.2 | −6.6 |
| 3.4 | 2.7 |

Note:
The chemical shift values (δ) are relative to that of tetramethyltin (SnMe$_4$).
The organometal compound content is the weight percentage (wt %) of the organometal compound in deuterated chloroform (CDCl$_3$).

TABLE 2

$^{119}$Sn-NMR chemical shift values obtained with respect to the sample solutions containing a degraded compound represented by formula (6), which is a tributyl metal compound
$^{119}$Sn-NMR data

| Alkoxy group (OR) | Chemical shift value (δ ppm) |
|---|---|
| Methoxy group | 109 |
| Ethoxy group | 102 |
| n-hexyloxy group | 100 |

Note:
The chemical shift values (δ) are relative to that of tetramethyltin (SnMe$_4$).

With respect to each step of the method of the present invention, detailed explanations are given below.

In step (1) of the method of the present invention, a reaction is performed between a first organometal compound mixture and carbon dioxide, wherein the first organometal compound mixture comprises a mixture of a reactive organometal compound having in its molecule at least two metal-oxygen-carbon linkages and an unregenerable unreactive compound which is derived from the reactive organometal compound and which has in its molecule at least three metal-carbon linkages, to thereby obtain a reaction mixture containing a carbonic ester formed by the reaction, the unregenerable unreactive compound, and a regenerable metamorphic organometal compound derived from the reactive organometal compound. Step (1) of the method of the present invention involves a reaction route in which a carbon dioxide adduct of a reactive organometal compound having in its molecule at least two metal-oxygen-carbon linkages is formed, and the adduct formed is thermally decomposed to obtain a carbonic ester. That is, in the reaction route of step (1), carbon dioxide is addition-bonded to a reactive organometal compound to form an adduct, and the adduct is thermally decomposed. Differing from the conventional methods, step (1) of the method of the present invention is characterized in that an organometal compound having in its molecule at least two metal-oxygen-carbon linkages is reacted with a small stoichiometric amount of carbon dioxide. In the conventional methods, carbon dioxide under a high pressure is reacted with an alcohol in the presence of a small amount of a metal catalyst. As an example of such conventional method, there can be mentioned a method in which carbon dioxide is reacted with methanol in the presence of dibutyltin dimethoxide (see Polyhedron, Vol. 19, pages 573-576 (2000)). In the conventional method described in this literature, carbon dioxide under a pressure of about 30 MPa is reacted with methanol at 180° C. in the presence of several millimoles of dibutyltin dimethoxide. The exact amount of carbon dioxide used in the reaction is not described in the above-mentioned literature. However, it is considered that, even if the partial pressure of methanol is subtracted, the amount of carbon dioxide used in the reaction should be as large as at least 100 times the stoichiometric amount relative to the amount of the organometal compound having a metal-oxygen-carbon linkage. By achieving the above-mentioned high pressure conditions, the equilibrium is forcibly displaced toward a carbonic ester, so that a carbonic ester can be produced in a yield which is higher than expected from the amount of the catalyst. However, by the reaction of carbon dioxide with methanol, free water is also produced, thus posing a serious problem in that the catalyst is hydrolyzed by the free water. For solving this problem, it is necessary to develop a method for dehydrating the reaction system. In the above-mentioned literature, it is described that, under the above-mentioned reaction conditions, dibutyltin oxide is produced as a hydrolysis product of dibutyltin dimethoxide and remains in the reaction system. Dibutyltin oxide cannot be dissolved in a solvent at room temperature; however, in the method of the present invention, even when the reaction mixture after completion of step (1) is cooled to room temperature, the reaction mixture generally remains in the form of a liquid. In this respect, the reaction used in the method of the present invention differs from the reaction used in the above-mentioned conventional method in which a large amount of carbon dioxide is used.

In the case of the conventional method, the reaction system has a high carbon dioxide concentration and, hence, the reaction is necessarily performed under high pressure conditions. Therefore, when the reaction mixture containing the produced carbonic ester is taken out from the reactor, it is necessary to purge a large amount of carbon dioxide from the reactor before taking out the reaction mixture. Such necessity poses problems not only in that a large amount of carbon dioxide is wasted, but also in that, if it is intended to reuse the purged carbon dioxide, repressurization of the carbon dioxide becomes necessary and, hence, a large amount of energy is consumed for the repressurization of the carbon dioxide. Further, in the conventional method, the following problem is also likely to occur. It is known that, when the reaction system has a high carbon dioxide concentration, the density of the carbon dioxide gas layer increases, so that the carbon dioxide dissolves not only a solvent and a catalyst but also the produced carbonic ester, thereby forming a reaction mixture comprised of a homogeneous mixture of carbon dioxide, the solvent, the catalyst and the produced carbonic ester. When the reaction mixture (homogeneous mixture) is cooled to obtain a liquid reaction mixture, the liquid reaction mixture contains carbon dioxide in the form of liquid carbonic acid. Thus, it is extremely difficult to separate the produced carbonic ester from the reaction mixture.

In step (1) of the method of the present invention, it is preferred that carbon dioxide is used in an amount which is 1 to 50 times, more advantageously 1 to 20 times, as large as the stoichiometric amount relative to the amount of the reactive organometal compound having in its molecule at least two metal-oxygen-carbon linkages. When the amount of carbon dioxide is large, the reaction becomes a high pressure reaction, so that not only does it become necessary to use a reactor having high pressure resistance, but also a large amount of carbon dioxide is wasted during purging of unreacted carbon dioxide after completion of step (1). Therefore, it is still more preferred that carbon dioxide is used in an amount which is 1 to 10 times as large as the stoichiometric amount relative to the amount of the reactive organometal compound. In other words, in step (1), it is preferred that the reactive organometal compound is used in an amount which is $1/50$ to 1 time, more advantageously $1/20$ to 1 time, as large as the stoichiometric amount relative to the amount of carbon dioxide. In the present invention, a carbon dioxide adduct of the reactive organometal compound having in its molecule at least two metal-oxygen-carbon linkages can be easily obtained by contacting the reactive organometal compound with carbon dioxide. When the reaction temperature is room temperature (20° C.), the carbon dioxide adduct is exothermically produced by contacting the reactive organometal compound with a stream of carbon dioxide having atmospheric pressure. In this case, the carbon dioxide adduct can be obtained in a yield of almost 100%. In accordance with the elevation of the reaction temperature, the amount of the carbon dioxide adduct produced becomes lowered; however, even when the reaction temperature is high, the lowering of the amount of the carbon dioxide adduct can be suppressed by contacting the reactive organometal compound with carbon dioxide having a high pressure. In step (1), when the reactive organometal compound is contacted with carbon dioxide having a high pressure, it is difficult to determine the amount of the carbon dioxide adduct produced; however, it is preferred that the reaction of the reactive organometal compound with carbon dioxide is performed under a desired pressure, depending on the rate at which the carbonic ester is produced and on the amount of the carbonic ester produced. The reaction pressure is generally from atmospheric pressure to 200 MPa. It is preferred that the amount of the carbonic ester obtained in step (1) is 100% or less, more advantageously 50% or less, based on the stoichiometric amount relative to the amount of the reactive organometal compound. The reason for this is as follows. The reactive organometal compound used in the method of the present invention is more susceptible to hydrolysis than the carbonic ester produced. Therefore, when the carbonic ester is obtained in an amount which is 100% or less, preferably 50% or less, based on the stoichiometric amount relative to the amount of the reactive organometal compound, water which is likely to hydrolyze the produced carbonic ester does advantageously not occur in the reaction mixture. On the other hand, in the case of the conventional methods, the reaction is performed so that the amount of the carbonic ester produced is more than 100%, based on the stoichiometric amount relative to the amount of the reactive organometal compound. As a result, in the case of the conventional methods, the generation of free water which is likely to hydrolyze the produced carbonic ester poses a serious problem. For preventing the produced carbonic ester from being hydrolyzed, it is necessary to add a dehydrating agent to the reaction system or to perform the reaction in the presence of a dehydrating agent, wherein the dehydrating agent is selected from the group consisting of a dehydrating agent which is more susceptible to hydrolysis than the reactive organometal compound, and a solid dehydrating agent having high water adsorptivity. Such use of a dehydrating agent is disadvantageous not only in that a complicated step is needed, but also in that the dehydrating agent is expensive. Therefore, the conventional methods have not been practically employed as a method for producing a carbonic ester on a commercial scale. By contrast, in the reaction route of step (1) of the method of the present invention, the main reaction is a decomposition reaction in which a carbon dioxide adduct of the reactive organometal compound having in its molecule at least two metal-oxygen-carbon linkages is thermally decomposed to obtain a carbonic ester. The thermal decomposition reaction is performed at a temperature in the range of from 20 to 300° C. In step (1) of the method of the present invention, an alcohol exchange reaction or an ester exchange reaction may be performed together with the above-mentioned decomposition reaction. Specifically, for example, when step (1) is performed in the presence of a second alcohol, an alcohol exchange reaction occurs between an oxygen-carbon linkage of the second alcohol and an oxygen-carbon linkage of the reactive organometal compound having in its molecule at least two metal-oxygen-carbon linkages, so that a carbonic ester corresponding to the second alcohol can be obtained. Alternatively, after the formation of a carbonic ester, a second alcohol may be added to the reaction system to perform an ester exchange reaction, thereby obtaining another carbonic ester corresponding to the second alcohol.

With respect to step (1), more detailed explanations are given below.

The studies by the present inventors have shown that, in step (1), a carbonic ester is obtained by the reaction between the reactive organometal compound and carbon dioxide. Therefore, the use of a second alcohol in step (1) is optional. However, from the viewpoint of producing a carbonic ester in high yield, it is preferred to use a second alcohol in step (1). The reason for this is as follows. The thermal decomposition reaction in step (1) has a reverse reaction. When a second alcohol is added to the reaction system, it is possible that another equilibrium reaction additionally occurs between the second alcohol and a thermal decomposition product other than the carbonic ester, thereby improving the yield of the carbonic ester. The addition of a second alcohol for improving the yield of the carbonic ester is especially effective when the reactive organometal compound is comprised mainly of an organometal compound represented by formula (2). On the other hand, when the reactive organometal compound is comprised mainly of an organometal compound represented by formula (1), the equilibrium of the thermal decomposition reaction in step (1) is biased toward the product system and, hence, the yield of the carbonic ester is considerably high, so that, in some cases, the yield of the carbonic ester cannot be further improved by the addition of a second alcohol. When the second alcohol contains a large amount of water, the yield of the carbonic ester is lowered. Therefore, it is preferred that the amount of water contained in the second alcohol is not more than 0.1 times, more advantageously not more than 0.01 times, as large as the stoichiometric amount relative to the amount of the reactive organometal compound. When the reaction in step (1) is performed using an organometal compound represented by formula (1), a carbon dioxide adduct of the organometal compound represented by formula (1) is thermally decomposed to produce a carbonic ester. It is well known that a carbonic ester is produced from a dimer of the organometal compound represented by formula (1) (see ECO INDUSTRY, Vol. 6, No. 6, pages 11-18 (2001)). In the conventional method described in this literature, a carbonic ester as well as dibutyltin oxide is produced from a dimer of the organometal compound represented by formula (1), wherein the amount of the carbonic ester produced is two molecules per molecule of the dimer of the organometal compound. The present inventors have made extensive and intensive studies on the formation of a carbonic ester from an organometal compound. As a result, it has surprisingly been found that, when a carbon dioxide adduct of a dimer of the organometal compound represented by formula (1) is thermally decomposed, a carbonic ester is swiftly eliminated wherein the amount of the carbonic ester eliminated is one molecule per molecule of the carbon dioxide adduct, so that an organometal compound represented by formula (2) and/or a carbon dioxide adduct thereof can be obtained. In this case, addition of an alcohol is not necessary. Step (2) may be performed immediately after there are obtained a carbonic ester and at least one compound selected from the group consisting of an organometal compound represented by formula (2) and a carbon dioxide adduct thereof. Alternatively, step (2) may be performed after a carbonic ester is further produced from the obtained organometal compound represented by formula (2) and/or the obtained carbon dioxide adduct thereof. As mentioned above, it is preferred that the reactive organometal compound used in step (1) comprises at least one compound selected from the group consisting of organometal compounds respectively represented by formulae (1) and (2). It is more preferred that at least a part of the reactive organometal compound used in step (1) is an organometal compound represented by formula (1). It is still more preferred that the reactive organometal compound used in step (1) contains 5 mol % or more of an organometal compound represented by formula (1), wherein the amount of the organometal compound is expressed in terms of the amount of a metal atom contained in the organometal compound.

A solvent for the reactive organometal compound may be used in step (1). The reactive organometal compound used in the present invention is generally in the form of a liquid. However, in some cases, the reactive organometal compound is in the form of a solid. Further, there is a case where the reactive organometal compound turns into a solid form when the reactive organometal compound becomes a carbon dioxide adduct thereof in step (1). Even when the reactive organometal compound is in the form of a solid, a carbonic ester can be produced in step (1). However, the fluidity of the reactive organometal compound is sometimes important when the carbonic ester is continuously produced. Further, for improving the rate of the reaction between the reactive organometal compound and carbon dioxide, it is sometimes preferred that the reactive organometal compound is in the form of a liquid. In such cases, step (1) may be performed using a solvent for the reactive organometal compound. As a solvent, there can be used an alcohol having the same organic group as in the carbonic ester produced. Alternatively, an inert solvent can also be used. Examples of inert solvents include hydrocarbons and ethers. Specific examples of inert solvents include $C_5$-$C_{20}$ saturated hydrocarbons, such as pentane, hexane, cyclohexane, heptane, octane and decane; $C_6$-$C_{20}$ aromatic hydrocarbons (which may have a $C_1$-$C_{14}$ saturated alkyl group and/or a $C_5$-$C_{14}$ cycloalkyl group), such as benzene, toluene, xylene and ethylbenzene; $C_6$-$C_{20}$ saturated alkyl ethers, such as dipropyl ether, dibutyl ether and dihexyl ether; $C_4$-$C_{20}$ cycloalkyl ethers, such as tetrahydrofuran and dioxane; and $C_7$-$C_{28}$ phenyl ethers (comprising a phenyl group having a $C_0$-$C_8$ substituent group, and a group selected from the group consisting of a $C_1$-$C_{14}$ alkyl group and a $C_5$-$C_{14}$ cycloalkyl group), such as anisole, ethyl phenyl ether, isopropyl phenyl ether, benzyl methyl ether and 4-methyl anisole.

The temperature employed for the reaction performed in step (1) is generally in the range of from room temperature (20° C.) to 300° C. When it is intended to complete the reaction in a short period of time, it is preferred to perform the reaction at 80 to 200° C. for 10 minutes to 500 hours. When the reaction in step (1) is performed at a high temperature (e.g., at 200° C. or more), the $^{119}$Sn-NMR chart obtained with respect to the reaction mixture after step (1) sometimes exhibits a peak ascribed to a certain substance around 100 ppm, wherein tetramethyltin is used as a reference in the $^{119}$Sn-NMR analysis. However, when the method of the present invention is repeatedly performed, it is preferred that the reaction in step (1) is performed under conditions wherein the formation of the above-mentioned substance exhibiting a peak around 100 ppm can be suppressed, or the reaction in step (1) is performed using an additive for suppressing the formation of the above-mentioned substance exhibiting a peak around 100 ppm.

With respect to the amount of carbon dioxide, when the reaction in step (1) is performed at room temperature (20° C.), it suffices if carbon dioxide is used in an amount which is the stoichiometric amount relative to the amount of the reactive organometal compound used in step (1). However, when the reaction in step (1) is performed at a temperature which is higher than room temperature (20° C.) under conditions wherein the amount of carbon dioxide is the stoichiometric amount relative to the amount of the reactive organometal compound used in step (1), the rate of the addition bonding of carbon dioxide to the reactive organometal compound sometimes becomes very low, so that the rate of the formation of the carbonic ester is markedly lowered. The pressure employed for the reaction performed in step (1) is generally from atmospheric pressure to 200 MPa, preferably from atmospheric pressure to 100 MPa, wherein, if desired, the reaction may be performed while introducing additional carbon dioxide into the reaction system or withdrawing a part of carbon dioxide from the reaction system. The introduction of additional carbon dioxide into the reaction system may be performed either intermittently or continuously.

In the method of the present invention, the reaction system in step (1) may contain substances other than mentioned above. Examples of other substances which are useful in step (1) include those which function as a dehydrating agent in the reaction system. By using a dehydrating agent in step (1), the reaction system can be maintained non-aqueous. As a dehydrating agent, any conventional organic dehydrating agent may be used. Examples of dehydrating agents include acetals and orthoesters, such as orthotrimethyl acetate. Further, dicyclohexylcarbodiimide and the like may also be used as an organic dehydrating agent. Alternatively, solid dehydrating agents, such as molecular sieves, may be used as a dehydrating agent. When a solid dehydrating agent is used, it is preferred that the solid dehydrating agent is removed from the reaction system before step (3) is performed.

In step (1) of the method of the present invention, an alcohol (second alcohol) is optionally used. From the viewpoint of improving the purity of the carbonic ester, as the second alcohol, it is preferred to use an alcohol having an organic group which is the same as the organic group of the oxy group (e.g., an alkoxy group or an aralkyloxy group) of the reactive organometal compound. When such an alcohol is used as the second alcohol, it is preferred that the amount of the second alcohol is 1 to 100,000 times the stoichiometric amount relative to the amount of the reactive organometal compound. On the other hand, when an alcohol having an organic group different from that of the oxy group of the reactive organometal compound is used as the second alcohol or when, as the reactive organometal compound, only an organometal compound of formula (2) is used, the amount of the second alcohol is preferably 2 to 1,000 times, more preferably 10 to 1,000 times, as large as the stoichiometric amount relative to the amount of the reactive organometal compound. When an alcohol having an organic group different from that of the oxy group of the reactive organometal compound is used as the second alcohol, an asymmetric carbonic ester is produced in step (1). As mentioned below, when a second alcohol is used in step (1), especially in the case where the organometal compound represented by formula (2) is used alone, the yield of the carbonic ester is greatly improved. The above-mentioned preferred amount of the second alcohol in the case where the organometal compound represented by formula (2) is used alone, is determined from this viewpoint.

In the case where the below-mentioned step (4) is followed by step (1), a second alcohol may be added to the reaction system so that the amount of the second alcohol falls within the above-mentioned preferred range. Alternatively, in such case where step (4) is followed by step (1), an alcohol may be removed from the reaction system.

As mentioned above, in step (1) of the method of the present invention, by performing a reaction between a first organometal compound mixture comprising a mixture of a reactive organometal compound and an unregenerable unreactive compound (which is derived from the reactive organometal compound) and carbon dioxide, there is obtained a reaction mixture containing a carbonic ester formed by the reaction, the unregenerable unreactive compound (i.e., the degraded compound) and a regenerable metamorphic organometal compound derived from the reactive organometal compound.

When it is confirmed by the analysis of the reaction mixture that a desired carbonic ester has been obtained, step (1) is finished. For example, when the carbonic ester is obtained in an amount which is 5% or more, based on the stoichiometric amount relative to the amount of the reactive organometal compound, step (1) may be finished. The reaction mixture may be taken out from the reactor, either after the pressure in the reactor is reduced to atmospheric pressure, or without lowering the pressure in the reactor. When step (1), step (2) and step (3) are performed in separate reactors, the reaction mixture may be continuously circulated by, for example, a method in which the reaction mixture after step (3) is fed to the reactor for step (1); the reaction mixture contained in the reactor for step (1) is fed to the reactor for step (2); and the reaction mixture contained in the reactor for step (2) is fed to the reactor for step (3). The circulation of the reaction mixture is preferred from the viewpoint of reducing the amount of carbon dioxide purged from the reactor (for step (1)) which has carbon dioxide filled therein. The reaction mixture obtained at completion of each step may be cooled or heated. When the reaction mixture is cooled, the reaction mixture may be forcibly cooled or allowed to cool spontaneously. As described below, if desired, step (1) for synthesizing a carbonic ester and step (2) for separating the synthesized carbonic ester can be simultaneously performed.

Step (2) of the method of the present invention is a step in which the reaction mixture obtained in step (1) is separated into a first portion containing the carbonic ester and the degraded compound (i.e., the unregenerable unreactive compound), and a second portion containing the regenerable metamorphic organometal compound. By such separation as to cause the degraded compound derived from the reactive organometal compound to be contained in the first portion containing the carbonic ester (wherein the first portion is taken out from the reaction system), it becomes possible to prevent the degraded compound from accumulating in the reaction system. Thus, all the problems of the conventional methods have been solved by the method of the present invention.

As described above, in the production of a carbonic ester from carbon dioxide and an alcohol by a conventional method using the reaction of formula (3), water as well as a carbonic ester is formed, and the water is contacted with an adsorbent or a dehydrating agent to remove the water from the reaction system, thereby displacing the equilibrium of the reaction toward the product system. Theoretically, the amount of a carbonic ester produced can also be increased by continuously removing the produced carbonic ester from the reaction system so as to displace the equilibrium of the reaction toward the product system. However, in the conventional method, when the produced carbonic ester is removed from the reaction system, water produced by the reaction accumulates in the reaction system. As is well known in the art, if water accumulates in the reaction system, the catalyst is hydrolyzed by the water and loses its catalyst activity. The hydrolyzed catalyst has very poor solubility in the solvent and, hence, poses a problem in that, in a subsequent dehydration step performed using an adsorption column, the hydrolyzed catalyst causes clogging of the adsorption column. Further, there has not been a method for regenerating the catalyst which has lost its catalyst activity by the hydrolysis thereof. For this reason, in the conventional methods, it has been impossible to efficiently separate the produced carbonic ester from the reaction mixture.

In step (2) of the method of the present invention, a conventional method for separating the carbonic ester from the reaction mixture can be used, so long as the effect of the method of the present invention is not impaired. For example, the separation of the carbonic ester from the reaction mixture can be performed by any of filtration, solvent extraction, distillation and membrane filtration, each of which is well known in the art. As a preferred example of an extraction solvent, there can be mentioned a solvent having no reactivity to the carbonic ester. Examples of such solvents include hydrocarbons, such as hexane and cyclohexane; aromatic hydrocarbons, such as benzene, toluene and chlorobenzene; and ethers, such as diethyl ether and anisole. The distillation can be performed by any conventional method. For example, the distillation can be performed by any of a distillation under atmospheric pressure, a distillation under reduced pressure, a distillation under superatmospheric pressure, and a thin film distillation, each of which is well known in the art. The temperature for the distillation varies depending on the type of the carbonic ester to be produced, but it is preferred that the temperature is from −20 to 200° C. The distillation may be performed either in the presence of a solvent or by extractive distillation. On the other hand, as mentioned above, when the distillation is performed under heating, the separation of the carbonic ester by distillation is sometimes accompanied by the following disadvantage. When the distillation is performed under heating, a reverse reaction of a carbonic ester and other thermal decomposition products in the equilibrium reaction is sometimes caused to occur, thereby lowering the yield of the carbonic ester. However, in such a case, when the first portion containing a carbonic ester having a high boiling point is separated from the reaction mixture by distillation, the carbonic ester can be obtained in high yield by separating the carbonic ester from the reaction mixture at a rate which is higher than the rate of the reverse reaction. For this purpose, it is preferred to perform the distillation under conditions wherein the distillation temperature and the degree of pressure reduction are appropriately adjusted.

In step (2), if desired, a third alcohol may be used. When a third alcohol is added to the reaction system, an ester exchange reaction occurs between the carbonic ester obtained in step (1) and the third alcohol to thereby obtain a carbonic ester which has a different number of carbon atoms from that of the carbonic ester obtained in step (1). The amount of the third alcohol used in step (2) is 1 to 1,000 times the stoichiometric amount relative to the amount of the reactive organometal compound used in step (1). The temperature employed for the ester exchange reaction is preferably in the range of from room temperature (about 20° C.) to 200° C. Taking into consideration the desired rate of the ester exchange reaction and the occurrence of a decomposition reaction of the carbonic ester at a high temperature, the temperature employed for the ester exchange reaction is more preferably in the range of from 50 to 150° C. In the ester exchange reaction, a conventional catalyst may be used. The ester exchange reaction and the separation of the carbonic ester from the reaction mixture may be performed either in a batchwise manner or simultaneously. As a method for separating the first portion containing the carbonic ester from the reaction mixture after the ester exchange reaction, any of the above-mentioned separation methods (such as filtration, solvent extraction, distillation and membrane filtration) can be used.

By the method of the present invention, not only a symmetric carbonic ester but also an asymmetric carbonic ester can be produced. In the case of the production of an asymmetric carbonic ester by using a conventional method, a symmetric carbonic ester is first produced, and the produced symmetric carbonic ester is then subjected to an ester exchange reaction to produce an asymmetric carbonic ester. On the other hand, in the method of the present invention, an asymmetric carbonic ester can be directly produced. Therefore, the method of the present invention is advantageous from the viewpoint of reducing the energy cost and reducing the facility construction cost. In the method of the present invention, an asymmetric carbonic ester can be produced as follows. Explanations are given below, taking as an example the case where the reactive organometal compound has at least one type of alkoxy group. When the reactive organometal compound used in step (1) has two different types of alkoxy groups, an asymmetric carbonic ester can be produced without use of alcohols (as a second alcohol and a third alcohol) in steps (1) and (2). On the other hand, when the organometal compound used in step (1) has only one type of alkoxy group, an asymmetric carbonic ester can be produced by performing step (1) in the presence of an alcohol (second alcohol) having an organic group which is different from the alkoxy group of the reactive organometal compound, or by performing step (2) in the presence of an alcohol (third alcohol) having an organic group which is different from the alkoxy group of the reactive organometal compound. Further, in each of the case where the reactive organometal compound used in step (1) has only one type of alkoxy group and the case where the reactive organometal compound used in step (1)

has two different types of alkoxy groups, an asymmetric carbonic ester can also be produced by performing step (1) in the presence of two different alcohols (second alcohols), or by performing step (2) in the presence of two different alcohols (third alcohols). When two different alcohols are used, the stoichiometric ratio of the two alcohols varies depending on the types of the two alcohols; however, the stoichiometric ratio is generally in the range of from 2:8 to 8:2, wherein each of the amounts of the two alcohols is expressed in terms of the stoichiometric amount relative to the amount of the reactive organometal compound. When it is intended to produce an asymmetric carbonic ester in an amount which is larger than that of a symmetric carbonic ester, it is preferred that the stoichiometric ratio of the two alcohols is as close to 1:1 as possible. Specifically, the stoichiometric ratio of the two alcohols is preferably in the range of from 3:7 to 7:3, more preferably in the range of from 4:6 to 6:4. When the production of an asymmetric carbonic ester is performed using two different alcohols which are used in excess amounts (for example, amounts each of which is at least 10 times the stoichiometric amount relative to the amount of the reactive organometal compound), it becomes possible to obtain an asymmetric carbonic ester having two different types of alkoxy groups corresponding to the two alcohols, irrespective of the type of the alkoxy group of the reactive organometal compound used in step (1). The separation of the first portion containing the asymmetric carbonic ester from the reaction mixture can be performed by any of the methods (such as filtration, solvent extraction, distillation and membrane filtration) described above in connection with step (2). In many cases, not only an asymmetric carbonic ester but also a symmetric carbonic ester is produced. In such cases, the following operation may be performed. The asymmetric and symmetric carbonic esters are separated from the first portion. The asymmetric carbonic ester is separated from the symmetric carbonic ester. The symmetric carbonic ester is either added to the second portion containing the regenerable metamorphic compound, followed by performing step (3), or returned to step (1) or (2).

As mentioned above, in step (2) of the method of the present invention, a mixture containing a degraded compound derived from the reactive organometal compound and the carbonic ester is separated from the reaction mixture as the first portion. With respect to the removal of the degraded compound, all of the degraded compound may be removed or a part of the degraded compound may be removed. The amount of the degraded compound removed may vary depending on the size of the reactor and/or the number of turnovers (i.e., the number of cycles of regeneration and reuse) of the reactive organometal compound. It is preferred that 10% or more of the degraded compound is removed. It is more preferred that 50% or more of the degraded compound is removed.

With respect to the separation method performed in step (2) of the method of the present invention, more detailed explanations are given below. The separation of the reaction mixture obtained in step (1) into the first portion, and the second portion can be performed by any of the above-mentioned conventional methods. As preferred examples of such methods, there can be mentioned a method in which water is added to the reaction mixture to effect a phase separation, and a method using distillation. Each of these methods are explained below.

1) A Separation Method in which Water is Added to the Reaction Mixture:

Water or a water-containing solvent is added to the reaction mixture obtained in step (1) to form a white slurry, and solids in the white slurry are removed by filtration. By the filtration, the second portion containing the regenerable metamorphic organometal compound can be obtained as a filtration residue and the first portion containing the carbonic ester and the degraded compound can be obtained as a filtrate. With respect to the water used in this method, there is no particular limitation; however, it is preferred to use a distilled water or a deionized water.

The amount of water used in step (2) is generally 1 to 100 times the stoichiometric amount relative to the amount of the reactive organometal compound used in step (1). The amount of water needed for separating the second portion (containing the regenerable metamorphic organometal compound) from the reaction mixture by phase separation is at most 1 times as large as the stoichiometric amount relative to the amount of the reactive organometal compound used in step (1).

In step (2), the temperature at which water is added to the reaction mixture obtained in step (1) is in the range of from a temperature (e.g., −20° C.) at which the water is not frozen in the reaction mixture to 100° C., preferably from 0 to 100° C., more preferably from 10 to 80° C. From the viewpoint of satisfactorily suppressing the occurrence of the hydrolysis of the carbonic ester, it is more preferred to adjust the temperature of water to 10 to 50° C. When water is used in step (2), water may be used alone or in combination with a solvent other than water. As a solvent other than water, it is preferred to use a solvent which does not react with the carbonic ester. In this case, when water is used in the form of a solution thereof in an alcohol which is the same as the second alcohol used in step (1), the separation of the solvent by the distillation becomes easy. When a third alcohol is used in step (2) to perform an ester exchange reaction, it is preferred that water is used in the form of a solution thereof in an alcohol which is the same as the alcohol present in the reaction mixture after the ester exchange reaction.

In step (2), when water is added to the reaction mixture, it is possible that the degraded compound also gradually undergoes hydrolysis, thus causing the solidification of the degraded compound. Therefore, it is preferred that, after the addition of water to the reaction mixture, the resultant white slurry is subjected to filtration as quickly as possible upon completion of the solidification of the second portion containing the regenerable metamorphic organometal compound. The period of time from the addition of water to the filtration varies depending on the types of the reactive organometal compound and alcohol used. When the separation in step (2) is performed at room temperature, the period of time is in the range of from 30 seconds to 60 minutes, preferably from 1 to 10 minutes.

2) A Separation Method Using Distillation

The reaction mixture obtained in step (1) is subjected to distillation to thereby separate the reaction mixture into the first portion containing the carbonic ester and the degraded compound and the second portion containing the regenerable metamorphic organometal compound. Each of the carbonic ester and the degraded compound has a boiling point lower than that of the regenerable metamorphic organometal compound. Therefore, the distillation can be performed by any conventional method. For example, the distillation can be performed by any of a distillation under superatmospheric pressure, a distillation under reduced pressure, a distillation under heating, a thin film distillation and a pervaporation using a membrane, each of which is well known in the art.

The temperature employed for the distillation is not particularly limited so long as the degraded compound has a vapor pressure at the temperature; however, the temperature is preferably from −20 to 300° C. From the viewpoint of minimizing the loss of the carbonic ester contained in the reaction mixture caused by the above-mentioned reverse reaction, it is more preferred that the temperature employed for distillation is from −20 to 200° C. For adjusting the temperature employed for distillation, the distillation may be performed either under superatmospheric pressure or under reduced pressure. Further, the distillation may be performed either in a continuous manner or in a batchwise manner.

The separation of the carbonic ester from the first portion (containing the carbonic ester and the unregenerable unreactive compound) obtained in step (2) can be performed easily by any of the conventional methods, such as adsorption, distillation, filtration and membrane separation.

Step (3) is a step of synthesizing (regenerating) a reactive organometal compound having in its molecule at least two metal-oxygen-carbon linkages. The compound in the second portion obtained in step (2) is generally in the form of a transparent or opaque liquid. For example, the second portion does not contain dibutyltin oxide in the form of a solid (it should be noted that dibutyltin oxide has no solubility in almost all organic solvents at room temperature (20° C.) and, hence, is in the form of a solid under such conditions). The structure of the compound in the second portion has not yet been identified. However, it has surprisingly been found that, by performing the reaction in step (3) of the method of the present invention, there can be obtained a reactive organometal compound having in its molecule at least two metal-oxygen-carbon linkages, such as an organometal compound represented by formula (1) or an organometal compound represented by formula (2).

Step (3) comprises reacting the second portion (of the reaction mixture) obtained in step (2) with a first alcohol to form a second organometal compound mixture and water and removing the water from the second organometal compound mixture, wherein the second organometal compound mixture comprises a mixture of a reactive organometal compound having in its molecule at least two metal-oxygen-carbon linkages and an unregenerable unreactive compound which is derived from the reactive organometal compound. If desired, the method of the present invention may further comprise, after step (3), a step (4) in which the second organometal compound mixture obtained in step (3) is recovered and recycled to step (1).

Examples of first alcohols used in step (3) include those which are exemplified above. If desired, prior to use of any of the above-mentioned alcohols, distillation of the alcohol may be performed for purifying the alcohol or adjusting the concentration of the alcohol. From this viewpoint, it is preferred to use an alcohol having a boiling point of 300° C. or lower as measured under atmospheric pressure. From the viewpoint of the ease in the removal of water in step (3), it is more preferred to use at least one alcohol selected from the group consisting of 1-butanol, 2-methyl-1-propanol, an alkyl alcohol having five or more carbon atoms, and an aralkyl alcohol having five or more carbon atoms.

With respect to the structure of a reactive organometal compound obtained by using a polyhydric alcohol as a first alcohol in step (3), there is no particular limitation. For example, the organometal compound may be comprised of at least one member selected from the group consisting of a crosslinked product of an organometal compound represented by formula (1) and a crosslinked product of an organometal compound represented by formula (2).

The amount of the first alcohol used in step (3) is preferably 1 to 10,000 times, more preferably 2 to 100 times, the stoichiometric amount relative to the amount of the reactive organometal compound used in step (1). When a sequence of steps (1) to (4) is repeated one or more times, it is sometimes possible that an alcohol is present in the second portion obtained in step (2). In such cases, an appropriate amount of an alcohol may be added to the second portion so that the amount of the alcohol in the second portion falls within the above-mentioned range of the amount of the first alcohol. Alternatively, the alcohol present in the second portion may be removed.

The removal of water in step (3) can be performed by any conventional method. For example, the removal of water in step (3) can be performed by any of distillation, a method using a dehydration column packed with a solid dehydrating agent (such as molecular sieves), and a method using membrane separation (such as pervaporation). Among them, distillation and a method using membrane separation (such as pervaporation) are preferred. It is well known that pervaporation can be used for the removal of water in an alcohol. In the present invention, pervaporation can be preferably used. In the case of an alcohol having a boiling point higher than that of water, the removal of water in the alcohol can also be easily performed by distillation under heating. On the other hand, in the case of an alcohol having a boiling point lower than that of water, the removal of water in the alcohol can also be performed by a distillation technique in which a solvent forming an azeotropic mixture with water is used. As mentioned above, the removal of water in the alcohol can be performed by any of a method using a solid dehydrating agent, distillation and membrane separation. However, when it is desired to obtain the second organometal compound mixture in a large amount in a short period of time, it is preferred that the removal of water in the alcohol is performed by distillation. The distillation can be performed by any conventional method. For example, the distillation can be performed by any of a distillation under atmospheric pressure, a distillation under reduced pressure, a distillation under superatmospheric pressure, a thin film distillation and an extractive distillation, each of which is well known in the art. The distillation can be performed at a temperature of from −20° C. to the boiling point of the first alcohol used in step (3). It is preferred that the distillation temperature is from 50° C. to the boiling point of the first alcohol used in step (3). Before or during the distillation, any desired substance may be added to the second portion of the second portion of the reaction mixture. The second portion of reaction mixture may contain, for example, a solvent which forms an azeotropic mixture with water from the viewpoint of the ease in the removal of water in step (3); or a solvent which enhances the hydrophobic property of the second portion of the reaction mixture so that the vapor-liquid equilibrium of the water formed by the reaction in step (3) becomes advantageous. Further, the second portion of the reaction mixture may contain a solvent which adjusts the fluidity of the second portion of the reaction mixture.

The temperature employed for the reaction performed in step (3) varies depending on the type of the first alcohol used; however, the temperature is generally from room temperature (about 20° C.) to 300° C. When the removal of water in step (3) is performed by distillation, the temperature employed for the distillation is not particularly limited so long as water has a vapor pressure at the temperature. When it is intended to complete the reaction in step (3) in a short period of time under atmospheric pressure, it is preferred that the distillation is performed under conditions wherein the temperature of the vapor formed by distillation is the azeotropic temperature of water and the first alcohol. When water and the first alcohol do not form an azeotropic mixture, it is preferred that the distillation is performed at the boiling point of water. When it is intended to complete the reaction in step (3) in a shorter period of time, the distillation may be performed, using an autoclave, at a temperature higher than the boiling point of the first alcohol or water while gradually removing water in the vapor phase. When the temperature employed for the reaction performed in step (3) is extremely high, it is sometimes possible that a thermal decomposition of the reactive organometal compound occurs. In such cases, a liquid containing water may be removed by reduced pressure distillation or the like.

Even when the first alcohol does not form an azeotropic mixture with water, water can be removed by azeotropic distillation in which a solvent forming an azeotropic mixture with water is used. This method is preferred since water can be removed at a low temperature. Examples of solvents which form an azeotropic mixture with water include unsaturated and saturated hydrocarbons, such as hexane, benzene, toluene, xylene, naphthalene; ethers, such as anisole and 1,4-dioxane; and halogenated hydrocarbons, such as chloroform. From the viewpoint of facilitating the separation of water from the azeotropic mixture after azeotropic distillation, it is preferred to use, as a solvent, an unsaturated or saturated hydrocarbon in which water has low solubility. When such a solvent is used, it is necessary to use the solvent in an amount such that water can be satisfactorily removed by azeotropic distillation. It is preferred to use a distillation column for the azeotropic distillation because the solvent can be recycled to the reaction system after separating the solvent from the azeotropic mixture in the distillation column and, hence, the amount of the solvent can be reduced to a relatively small one.

By performing the reaction in step (3), there can be obtained, for example, an organometal compound mixture containing at least one reactive organometal compound selected from the group consisting of an organometal compound represented by formula (1) and an organometal compound represented by formula (2).

When the reaction in step (3) reaches a stage where almost no water is generated, step (3) can be finished. When a sequence of steps (1) to (4) is repeated one or more times, the amount of the carbonic ester obtained in step (1) varies depending on the amount of water which is removed in step (3). Therefore, it is preferred that the amount of water removed in step (3) is as large as possible.

Generally, the amount of water removed in step (3) is 0.01 to 1 times as large as the amount of water produced by the reaction in step (3), wherein the amount of water produced is theoretically calculated based on the assumption that only an organometal compound represented by formula (1) is produced by the reaction in step (3). In many cases, the amount of water removed in step (3) is less than 1 times as large as the above-mentioned theoretical amount of water produced by the reaction in step (3). As a result of the studies made by the present inventors, it has been found that, when an organometal compound is produced from dibutyltin oxide and an alcohol and a sequence of steps (1) to (4) is repeated one or more times, the amount of water removed in step (3) is less than the amount of water generated during the reaction in which the reactive organometal compound is produced from dibutyltin oxide and an alcohol. When, in step (2), water is added to the reaction system for separating the first portion containing the carbonic ester and the degraded compound, it is sometimes possible that a white solid containing water is obtained and the amount of water removed in step (3) is more than 1 times the above-mentioned theoretical amount of water produced by the reaction in step (3). When a sequence of steps (1) to (4) is repeated one or more times, it is difficult to calculate a theoretical amount of water produced by the reaction performed in step (3) because the structure of the regenerable metamorphic organometal compound contained in the reaction mixture obtained in step (1) has not yet been identified. In this case, the change (with time) in the amount of water which is removed is measured. When it is confirmed by the measurement that almost no more water is removed, step (3) may be finished.

After completion of step (3), if desired, an excess amount of the alcohol may be removed. From the viewpoint of improving the purity of the carbonic ester obtained in step (1) in the case where a sequence of steps (1) to (4) is repeated one or more times, it is preferred to remove an excess amount of the alcohol. When the same alcohol as used in step (3) is used in step (1) in the case where a sequence of steps (1) to (4) is repeated one or more times, the removal of the alcohol after step (3) may not be performed. Further, an appropriate amount of the alcohol may be added to the reaction system after step (3).

The removal of an excess amount of the alcohol can be performed as follows. When the second organometal compound mixture obtained in step (3) is in the form of a solid, the alcohol can be removed as a filtrate obtained by filtration. On the other hand, when the second organometal compound mixture obtained in step (3) is in the form of a liquid, the removal of the alcohol can be performed by a distillation under reduced pressure, or by a method in which an inert gas, such as nitrogen, is introduced into the reactor so that the alcohol is removed in an amount which corresponds to the vapor pressure of the alcohol. In the case of using an inert gas, when the inert gas is not completely dried, a disadvantage is likely to occur wherein the second organometal compound mixture is hydrolyzed and decomposed into a metal oxide and an alcohol, so that the amount of the carbonic ester obtained by the reaction in step (1) in the case where a sequence of steps (1) to (4) is repeated one or more times, becomes extremely lowered. Steps (1) to (3) may be performed either intermittently or in a batchwise manner.

As described above, if desired, steps (1) and (2) can be simultaneously performed. Also, if desired, steps (2) and (3) can be simultaneously performed. Further, steps (1) to (3) can also be simultaneously performed. Further, when the method of the present invention is repeated one or more times, if desired, step (3) and step (1) of the subsequent cycle can be simultaneously performed. With respect to the cases where these steps are simultaneously performed, explanations are given below.

(The Case where Steps (1) and (2) are Simultaneously Performed)

With respect to the reaction performed in step (1), there are two cases: one (first case) is the case where a liquid phase and a vapor phase are present during the performance of the reaction in step (1), and the other (second case) is the case where carbon dioxide is in a supercritical state under high temperature and high pressure conditions and the reaction mixture forms a homogeneous mixture. Steps (1) and (2) can be simultaneously performed in the first case. In the first case, the reaction temperature and reaction pressure vary depending on the type of an alkoxy group contained in the reactive organometal compound and the type of an alcohol when an alcohol is used. However, the reaction temperature is generally 200° C. or lower and the reaction pressure is 8 MPa or less. The carbonic ester has high solubility in carbon dioxide and, hence, a part of the carbonic ester is dissolved in the vapor phase. Therefore, by performing the reaction in step (1) while withdrawing a part of the vapor phase, the first portion (containing the carbonic ester and the unregenerable unreactive compound) can be separated from the reaction mixture.

(The Case where Steps (2) and (3) are Simultaneously Performed)

Steps (2) and (3) can be simultaneously performed when the reactive organometal compound is obtained from an alcohol having a boiling point higher than that of water, and a $C_1$-$C_3$ alkyl alcohol is used in step (1) or (2). The separation of the carbonic ester, the degraded compound and water from the reaction mixture can be performed by a method in which the reaction mixture obtained in step (1) is placed under a stream of an inert gas, such as carbon dioxide gas, thereby removing the carbonic ester, the degraded compound and water from the reaction mixture, in such a form as entrained by the inert gas. The separation of the carbonic ester, the degraded compound and water from the reaction mixture can also be performed by a conventional method, such as membrane separation. By such a method, the carbonic ester, the degraded compound and water can be continuously separated from the reaction mixture.

(The Case where Steps (1) to (3) are Simultaneously Performed)

With respect to the reaction performed in step (1), there are two cases: one (first case) is the case where a liquid phase and a vapor phase are present during the performance of the reaction in step (1), and the other (second case) is the case where carbon dioxide is in a supercritical state under high temperature and high pressure conditions and the reaction mixture forms a homogeneous mixture. Steps (1) to (3) can be simultaneously performed in the case where a liquid phase and a vapor phase are present during the performance of the reaction in step (1), the reactive organometal compound is obtained from an alcohol having a boiling point higher than that of water, and a $C_1$-$C_3$ alkyl alcohol (preferably methanol or ethanol) is used. In this case, the reaction temperature and reaction pressure vary depending on the type of an alkoxy group contained in the reactive organometal compound and the type of an alcohol when an alcohol is used. However, the reaction temperature is generally 150° C. or less and the reaction pressure is generally 5 MPa or less. Water, the carbonic ester and the degraded compound have high solubility in carbon dioxide and, hence, a part of each of the water, the carbonic ester and the degraded compound is dissolved in the vapor phase. Therefore, by performing the reaction in step (1) while withdrawing a part of the vapor phase, the carbonic ester and the degraded compound can be separated from the reaction mixture while regenerating the organometal compound. Further, it is also possible to employ a method in which the reaction is performed in a fixed-bed reactor containing an organometal compound mixture, wherein the organometal compound mixture is supported on a carrier or in the form of a solid. In this method, carbon dioxide and a $C_1$-$C_3$ alcohol are introduced into the fixed-bed reactor to effect a reaction, thereby obtaining a carbonic ester, a degraded compound and water in such a form as entrained by carbon dioxide gas. As a carrier for supporting the organometal compound mixture, a conventional carrier can be used.

(The Case where Step (3) and Step (1) of the Subsequent Cycle are Simultaneously Performed when the Method of the Present Invention is Repeated One or More Times)

When the method of the present invention is repeated one or more times, step (3) and step (1) of the subsequent cycle can be simultaneously performed by a method in which step (3) is performed in an atmosphere of or in the presence of carbon dioxide gas. Specifically, step (3) and step (1) of the subsequent cycle can be simultaneously performed by a method in which the second portion (of the reaction mixture) obtained in step (2) is reacted with a first alcohol to regenerate (resynthesize) a reactive organometal compound and generate water, and the regenerated reactive organometal compound is reacted with carbon dioxide to thereby obtain a carbonic ester, wherein the water generated is removed. Step (3) and step (1) of the subsequent cycle can be simultaneously performed in the case where a liquid phase and a vapor phase are present in the reaction system. In this case, the reaction temperature and reaction pressure vary depending on the type of an alkoxy group contained in the reactive organometal compound and the type of an alcohol used. However, the reaction temperature is generally 200° C. or lower and the reaction pressure is 1 MPa or less. It is preferred that step (3) and step (1) of the subsequent cycle are performed simultaneously by reacting the reactive organometal compound with carbon dioxide in the presence of an alcohol having a boiling point higher than 100° C. (as measured under atmospheric pressure) under conditions wherein the reaction temperature is the same or lower than the boiling point of the alcohol and the pressure is from atmospheric pressure to 0.5 MPa. It is more preferred that step (3) and step (1) of the subsequent cycle are performed simultaneously by a method in which carbon dioxide gas is introduced into the second portion of the reaction mixture so that the water generated is withdrawn from the reaction system in such a form as entrained by carbon dioxide gas.

As mentioned above, the method of the present invention may further comprise, after step (3), a step (4) in which the second organometal compound mixture obtained in step (3) is recovered and recycled to step (1). A sequence of steps (1) to (4) can be repeated one or more times. Prior to the recycle of the organometal compound to step (1), the organometal compound may be cooled or heated. The step (4) can be performed either continuously or in a batchwise manner.

In step (3), when the reaction of the second portion of the reaction mixture with a first alcohol is performed at a high temperature or for a prolonged period of time, a problem arises in that the degraded compound is formed in a large amount. Therefore, it is preferred that the reaction in step (3) is performed under conditions wherein the formation of the degraded compound is suppressed as much as possible. The degraded compound (i.e., the unregenerable unreactive compound) is formed by a disproportionation reaction which is caused to occur when the organometal compounds respectively represented by formulae (1) and (2) are heated. In a carbon dioxide atmosphere, such disproportination reaction progresses slowly and, hence, the unregenerable unreactive compound is formed mainly in this step (3). With respect to the degraded compound formed and accumulated prior to the reaction of step (3), and the degraded compound being formed during the reaction in step (3), these degraded compounds can be removed from the reaction system in step (3). The reason is that the degraded compound represented by formula (6) above has a boiling point lower than that of the reactive organometal compound obtained by the reaction of step (3). The removal of the degraded compound from the reaction system in step (3) can be performed by a conventional method, such as distillation or membrane separation. For example, the distillation can be preferably performed by any of a distillation under superatmospheric pressure, a distillation under reduced pressure, a distillation under heating and a thin film distillation. The membrane separation can be preferably performed by, for example, a pervaporation using a membrane. From the viewpoint of minimizing the number of steps of the removal method employed, it is more preferred that the removal of the degraded compound is performed by a method in which, after the water is removed in step (3), the degraded compound is distilled off under greatly reduced pressure. The temperature employed for the distillation is not particularly limited so long as the degraded compound has a vapor pressure at the temperature; however, the temperature is preferably from about 20° C. to 300° C. When the distillation is performed under heating at a high temperature, there is a danger that the amount of the degradation compound formed further increases. Therefore, it is more preferred that the temperature employed for distillation is from 20 to 200° C.

In the method of the present invention, a solid degraded compound (other than the above-mentioned unregenerable unreactive compound) which has in its molecule at least three metal-carbon linkages is sometimes formed. It is presumed that such solid degraded compound is derived from a disproportionation reaction product which is formed as a counterpart of the unregenerable unreactive compound having in its molecule at least three metal-carbon linkages. As an example of such solid degraded compound, there can be mentioned a metal oxide, such as titanium oxide or tin oxide. These solid degraded compounds can be easily removed from the reaction system by filtration. In step (1), step (2) (in the case where water is not used) and step (3), the reaction mixture is generally present in the form of a homogeneous liquid. Therefore, when solid degraded compounds are precipitated in the reaction system as a result of a repetitious use of the organometal compound, the solid degraded compounds can be removed by filtration. The filtration can be performed by any of the conventional methods. For example, the filtration can be performed by any of a filtration under atmospheric pressure, a filtration under reduced pressure, a filtration under superatmospheric pressure and a centrifugation. When water intrudes into the reaction system during the filtration, there is a danger that the useful organometal compound is hydrolyzed and solidified. Therefore, for preventing the useful organometal compound from being removed together with the solid degraded compound, it is preferred that the filtration is performed with a considerable care so as to suppress the occurrence of the hydrolysis of the organometal compound.

Hereinbelow, explanations are given with respect to the reaction vessels used in the method of the present invention.

With respect to the type of the reaction vessel used in each of steps (1), (2) and (3), there is no particular limitation, and any conventional reaction vessel can be used. Examples of conventional reaction vessels include a stirring vessel, a multi-stage stirring vessel and a continuous multi-stage distillation column. These reaction vessels can be used individually or in combination. Using at least one of the above-mentioned reaction vessels, steps (1) to (3) may be performed in a batchwise or continuous manner. Specifically, with respect to steps (1) and (3), from the viewpoint of efficiently displacing the equilibrium of the reaction in the direction of the product system, it is preferred to use a multi-stage distillation column. It is more preferred that each of steps (1) and (3) is continuously performed using a multi-stage distillation column.

With respect to the multi-stage distillation column, there is no particular limitation so long as it is a distillation column which has two or more theoretical stages and which is capable of continuous distillation. As such a multi-stage distillation column, any conventional multi-stage distillation column which is generally used in the art can be used. Examples of such multi-stage distillation columns include plate type columns using a tray, such as a bubble-cap tray, a sieve tray, a valve tray or a counterflow tray; and packed type columns packed with any of various packings, such as a Raschig ring, a Lessing ring, a Pall ring, a Berl saddle, an Interlox saddle, a Dixon packing, a McMahon packing, a Heli pack, a Sulzer packing and Mel-lapak. Further, a mixed type of plate column and packed column, which comprises both a plate portion and a portion packed with packings, can also be preferably used.

BEST MODE FOR CARRYING OUT THE INVENTION

Hereinbelow, the present invention will be described in more detail with reference to the following Examples, which should not be construed as limiting the scope of the present invention.

Methods for Analyses (1) Nuclear Magnetic Resonance (NMR) Analysis of an Organometal Compound Apparatus: JNM-A400 FT-NMR system (manufactured and sold by JEOL Ltd., Japan)

Preparation of sample solutions for $^1$H—, $^{13}$C— and $^{119}$Sn-NMR analyses:

About 0.1 to 1 g of a reaction mixture was weighed, and then 0.05 g of tetramethyltin and about 0.85 g of deuterated chloroform were added thereto, thereby obtaining a sample solution for an NMR analysis.

(2) Gas Chromatography (GC) Analysis of a Carbonic Ester

Apparatus: GC-2010 system (manufactured and sold by Shimadzu Corporation, Japan).

(i) Preparation of a Sample Solution 0.06 g of a reaction mixture was weighed, and then about 2.5 ml of dehydrated dimethylformamide or dehydrated acetonitrile was added thereto. Further, to the resultant was added about 0.06 g of diphenyl ether as an internal standard, thereby obtaining a sample solution for a GC analysis.

(ii) Conditions for a GC Analysis

Column: DB-1 (manufactured and sold by J & W Scientific, U.S.A.)

Liquid phase: 100% dimethyl polysiloxane

Column length: 30 m

Column diameter: 0.25 mm

Film thickness: 1 µm

Column temperature: the temperature was elevated from 50° C. to 300° C. at a rate of 10° C./min.

Injection temperature: 300° C.

Detector temperature: 300° C.

Detector: FID (flame ionization detector)

(iii) Quantitative Analysis

The quantitative analysis of a sample solution was performed using a calibration curve obtained with respect to standard samples.

(3) Calculation of the Yield of a Carbonic Ester (i.e., Dialkyl Carbonate)

The yield of a dialkyl carbonate was expressed in terms of the mol % of the dialkyl carbonate, based on the molar amount of the organometal compound used in step (1), wherein the amount of the organometal compound is expressed in terms of the amount of a metal atom contained therein.

EXAMPLE 1

First, a reactive organometal compound having a 2-ethylhexyloxy group was synthesized from dibutyltin oxide and 2-ethyl-1-hexanol as follows.

Into a 1-liter four-necked flask equipped with a cooling tube, a thermometer (for the measurement of the internal temperature of the flask), a vacuum pump and a vacuum controller (manufactured and sold by Okano Works, Ltd., Japan) were charged 249 g (1.0 mol) of dibutyltin oxide (manufactured and sold by Aldrich, U.S.A.), 650 g (5.0 mol) of 2-ethyl-1-hexanol (manufactured and sold by Aldrich, U.S.A.; a dehydrated grade). Further, a stirrer was placed in the flask. The flask was immersed in an oil bath. The atmosphere in the flask was purged with nitrogen gas. Then, stirring of the contents of the flask was started while heating. When the internal temperature of the flask reached 172° C., the pressure in the flask was gradually reduced while withdrawing a distillate (i.e., water and 2-ethyl-1-hexanol) from the flask by means of a purge line, and a reaction was performed for about 7 hours. By reducing the pressure in the flask, the pressure in the flask was finally lowered to about 28 KPa. When the distillate was almost thoroughly withdrawn from the flask, the flask was taken out from the oil bath, and the inside of the flask was cooled. Then, nitrogen gas was introduced into the flask to elevate the pressure in the flask to atmospheric pressure. By the above-mentioned operation, 410 g of a viscous liquid was obtained.

The distillate withdrawn from the flask was analyzed. As a result, it was found that the distillate contained about 13 g of water. The above-obtained viscous liquid was analyzed by $^1$H—, $^{13}$C— and $^{119}$Sn-NMR's. As a result, it was found that the viscous liquid contained 1,1,3,3-tetrabutyl-1,3-di(2-ethylhexyloxy)distannoxane, dibutyltin di(2-ethylhexyloxide) and tributyltin(2-ethylhexyloxide).

Step (1)

404 g of the above-obtained viscous liquid was charged into a 500-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having a pressure of 4 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 3 hours while maintaining the internal pressure of the autoclave at 4 MPa by means of a back-pressure valve of the carbon dioxide gas bomb. After the reaction, the inside of the autoclave was cooled to about 30° C., and carbon dioxide gas was gently purged therefrom through the purge line to lower the pressure in the autoclave to atmospheric pressure, thereby obtaining a transparent liquid as a reaction mixture. It was found that the yield of di(2-ethylhexyl)carbonate was 25%. The reaction mixture was analyzed by $^1$H—, $^{13}$C— and $^{119}$Sn-NMR's. As a result, it was confirmed that the reaction mixture contained tributyltin(2-ethylhexyloxide) and a carbon dioxide adduct thereof in a total amount of about 0.1 mol %. These two compounds are unregenerable unreactive compounds.

Step (2)

After step (1), a thin film distillation apparatus (E-420; manufactured and sold by Shibata Scientific Technology Ltd., Japan) having an internal temperature of 130° C. and an internal pressure of about 65 Pa was connected to the autoclave through a liquid transferring pump (LC-10AT; manufactured and sold by Shimadzu Corporation, Japan), and a distillation was performed as follows. About 120 g of the reaction mixture obtained in step (1) was charged into the thin film distillation apparatus through the liquid transferring pump at a rate of 3 g/min to distill off the volatile matter from the reaction mixture, followed by cooling, thereby recovering about 14 g of the volatile matter in a liquid form. It was found that about 50% of the di(2-ethylhexyl)carbonate contained in the reaction mixture charged into the thin film distillation apparatus was distilled off as a volatile matter. The volatile matter in a liquid form was analyzed by $^1$H—, $^{13}$C— and $^{119}$Sn-NMR's. As a result, it was confirmed that the volatile matter in a liquid form contained about 0.02 mol of tributyltin (2-ethylhexyloxide).

Step (3)

Into a 300-ml four-necked flask equipped with a cooling tube, a thermometer (for the measurement of the internal temperature of the flask), a vacuum pump and a vacuum controller (manufactured and sold by Okano Works, Ltd., Japan) were charged about 100 g of the distillation residue obtained by the above-mentioned distillation, 5 g (about 2 mmol) of dibutyltin oxide (manufactured and sold by Aldrich, U.S.A.), and 216 g (1.7 mol) of 2-ethyl-1-hexanol (manufactured and sold by Aldrich, U.S.A.; a dehydrated grade). Further, a stirrer was placed in the flask. The flask was immersed in an oil bath. The atmosphere in the flask was purged with nitrogen gas. Then, stirring of the contents of the flask was started while heating. When the internal temperature of the flask reached 172° C., the pressure in the flask was gradually reduced while withdrawing a distillate (i.e., water and 2-ethyl-1-hexanol) from the flask by means of a purge line, and a reaction was performed for about 7 hours. By reducing the pressure in the flask, the pressure in the flask was finally lowered to about 28 KPa. When the distillate was almost thoroughly withdrawn from the flask, the flask was taken out from the oil bath, and the inside of the flask was cooled. Then, nitrogen gas was introduced into the flask to elevate the pressure in the flask to atmospheric pressure. By the above-mentioned operation, a viscous liquid was obtained.

The above-obtained viscous liquid was analyzed by $^1$H—, $^{13}$C— and $^{119}$Sn-NMR's. As a result, it was found that the viscous liquid contained 1,1,3,3-tetrabutyl-1,3-di(2-ethylhexyloxy)distannoxane, dibutyltin di(2-ethylhexyloxide) and tributyltin(2-ethylhexyloxide). Of these three compounds, the first two compounds are regenerable metamorphic organometal compounds and the last one compound is an unregenerable unreactive compound.

The viscous liquid obtained in step (3) above was recovered and recycled to step (1), and step (1) was performed as follows.

79 g of the above-obtained viscous liquid was charged into a 100-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having a pressure of 4 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 3 hours while maintaining the internal pressure of the autoclave at 4 MPa by means of a back-pressure valve of the carbon dioxide gas bomb. After the reaction, the inside of the autoclave was cooled to about 30° C., and carbon dioxide gas was gently purged therefrom through the purge line to lower the pressure in the autoclave to atmospheric pressure, thereby obtaining a transparent liquid as a reaction mixture. It was found that the yield of di(2-ethylhexyl)carbonate was 25%.

After step (1), a thin film distillation apparatus (E-420; manufactured and sold by Shibata Scientific Technology Ltd., Japan) having an internal temperature of 130° C. and an internal pressure of about 65 Pa was connected to the autoclave through a liquid transferring pump (LC-10AT; manufactured and sold by Shimadzu Corporation, Japan), and a distillation was performed as follows. About 25 g of the reaction mixture obtained in step (1) was charged into the thin film distillation apparatus through the liquid transferring pump at a rate of 3 g/min to distill off the volatile matter from the reaction mixture, followed by cooling, thereby recovering about 14 g of the volatile matter in a liquid form. It was found that about 50% of the di(2-ethylhexyl)carbonate contained in the reaction mixture charged into the thin film distillation apparatus was distilled off as a volatile matter. The volatile matter in a liquid form was analyzed by $^1$H—, $^{13}$C— and $^{119}$Sn-NMR's. As a result, it was confirmed that the volatile matter in a liquid form contained about 0.005 mol of tributyltin(2-ethylhexyloxide).

EXAMPLE 2

Synthesis of an organometal compound having a hexyloxy group from dibutyltin oxide and hexanol was performed as follows.

Into a 200-ml autoclave (manufactured and sold by Toyo Koatsu Co., Ltd., Japan) were charged 24.9 g (100 mmol) of dibutyltin oxide (manufactured and sold by Aldrich, U.S.A.) and 51.1 g (500 mmol) of hexanol (manufactured and sold by Aldrich, U.S.A.; a dehydrated grade). The autoclave was sealed. The atmosphere in the autoclave was purged with nitrogen gas. Then, stirring of the contents of the autoclave was started, and the internal temperature of the autoclave was elevated to 160° C. Then, the stirring was continued for about 30 minutes. Thereafter, the valve of the purge line of the autoclave was opened, and water and hexanol was distilled off through the purge line over 4 hours while blowing a small amount of nitrogen gas into the bottom of the autoclave. After that period, there was almost no distillate any more. Then, the inside of the autoclave was cooled to about 30° C., and there was obtained a viscous reaction mixture. $^1$H—, $^{13}$C— and $^{119}$Sn-NMR analyses of the reaction mixture was performed. The NMR analyses showed that the viscous reaction mixture contained about 40 mmol of 1,1,3,3-tetrabutyl-1,3-di-hexyloxy-di-stannoxane, about 6 mmol of dibutyltin dihexyloxide and about 4 mml of tributyltin hexyloxide.

Step (1)

Into the above-mentioned 200-ml autoclave containing the reaction mixture (containing an organometal compound having a hexyloxy group) was charged 61.5 g (602 mmol) of hexanol (manufactured and sold by Aldrich, U.S.A.; a dehydrated grade), and the autoclave was sealed. Then, from a carbon dioxide gas bomb which was connected to the autoclave through a SUS tube and a valve, carbon dioxide gas having a pressure of 5 MPa was introduced into the autoclave. Stirring of the contents of the autoclave was started. 10 Minutes after the start of the stirring, the valve of the carbon dioxide gas bomb was closed. Then, the internal temperature of the autoclave was elevated to 180° C. while stirring. In this instant, the internal pressure of the autoclave was about 7.5 MPa. Then, a reaction was performed for 6 hours while maintaining the internal pressure of the autoclave at about 7.5 MPa. Thereafter, the inside of the autoclave was cooled to about 30° C. and the internal pressure of the autoclave was returned to atmospheric pressure by gently purging the carbon dioxide gas, and there was obtained a transparent reaction mixture. In the reaction mixture, dihexyl carbonate was obtained in a yield of 14%.

Step (2)

After step (1), 10 g of hexanol containing 1% of water was gently added to the reaction mixture obtained in step (1), and the resultant mixture was stirred for about 1 minute. Then, the autoclave was opened, and it was found that the mixture in the autoclave had turned into a white slurry. The white slurry was subjected to filtration using a membrane filter (H020A142C, manufactured and sold by Advantec Toyo Kaisha, Ltd., Japan) to thereby obtain white solids and a filtrate. The white solids were washed 2 times with 20 ml of hexanol. The filtrate was transferred into a 1-liter eggplant-shaped flask and subjected to a distillation under heating in an oil bath at 160° C. and under reduced pressure. By the distillation, hexanol, tributyltin hexyloxide and dihexyl carbonate were recovered as a distillate. The yield of dihexyl carbonate was 13%. It was found that the distillate contained about 2 mmol of tributyltin hexyloxide. On the other hand, a viscous liquid remained in the flask after completion of the distillation.

Step (3)

The white solids obtained in step (2) and the residual viscous liquid which remained in the flask after the distillation performed in step (2), were charged into a 200-ml autoclave (manufactured and sold by Toyo Koatsu Co., Ltd., Japan). Further, 51.1 g (500 mmol) of hexanol (manufactured and sold by Aldrich, U.S.A.; a dehydrated grade) was charged into the autoclave, and the autoclave was sealed. The atmosphere in the autoclave was purged with nitrogen gas. Then, stirring of the contents of the autoclave was started, and the internal temperature of the autoclave was elevated to 160° C. Then, the stirring was continued for about 30 minutes. Thereafter, the purge line of the autoclave was opened, and water and hexanol were distilled off through the purge line over 4 hours while blowing a small amount of nitrogen gas into the bottom of the autoclave. After that period, there was almost no distillate any more. Then, the inside of the autoclave was cooled to about 30° C., and there was obtained a reaction mixture. $^1$H—, $^{13}$C— and $^{119}$Sn-NMR analyses of the reaction mixture was performed. The NMR analyses showed that the reaction mixture contained about 40 mmol of 1,1,3,3-tetrabutyl-1,3-di-hexyloxy-distannoxane, about 7 mmol of dibutyltin dihexyloxide and about 4 mmol of tributyltin hexyloxide.

After step (3), step (1) was performed as follows.

Into the above-mentioned autoclave in which step (3) was performed was charged 61.5 g (602 mmol) of hexanol (manufactured and sold by Aldrich, U.S.A.; a dehydrated grade). The autoclave was sealed. Then, from a carbon dioxide gas bomb which was connected to the autoclave through a SUS tube and a valve, carbon dioxide gas having a pressure of 5 MPa was introduced into the autoclave. Stirring of the contents of the autoclave was started. 10 Minutes after the start of the stirring, the valve of the carbon dioxide gas bomb was closed. Then, the internal temperature of the autoclave was elevated to 180° C. while stirring. In this instant, the internal pressure of the autoclave was about 7.5 MPa. Then, a reaction was performed for 6 hours while maintaining the internal pressure of the autoclave at about 7.5 MPa. Thereafter, the inside of the autoclave was cooled to about 30° C. and the internal pressure of the autoclave was returned to atmospheric pressure by gently purging the carbon dioxide gas through the purge line, and there was obtained a transparent reaction mixture. In the reaction mixture, dihexyl carbonate was obtained in a yield of 14%.

After step (1), 10 g of hexanol containing 1% of water was gently added to the reaction mixture obtained in step (1), and the resultant mixture was stirred for about 1 minute. Then, the autoclave was opened, and it was found that the mixture in the autoclave had turned into a white slurry. The white slurry was subjected to filtration using a membrane filter (H020A142C, manufactured and sold by Advantec Toyo Kaisha, Ltd., Japan) to thereby obtain white solids and a filtrate. The white solids were washed 2 times with 20 ml of hexanol. The filtrate was transferred into a 1-liter eggplant-shaped flask and subjected to a distillation under heating in an oil bath at 160° C. and under reduced pressure. The resultant flask was subjected to distillation under heating and under reduced pressure. By the distillation, hexanol, tributyltin hexyloxide and dihexyl carbonate were recovered as a distillate. The yield of dihexyl carbonate was 13%. It was found that the distillate contained about 2 mmol of tributyltin hexyloxide.

EXAMPLE 3

First, a reactive organometal compound having a 3-methylbutoxy group was synthesized from dibutyltin oxide and 3-methyl-1-butanol as follows.

Into a 1-liter four-necked flask equipped with a cooling tube (which was connected with a vacuum controller and a vacuum pump) and a Dean-Stark trap were charged 70.5 g (0.28 mol) of dibutyltin oxide (manufactured and sold by Aldrich, U.S.A.) and 502 g (5.7 mol) of 3-methyl-1-butanol (manufactured and sold by Aldrich, U.S.A.). Further, a stirrer was placed in the flask.

The flask was immersed in an oil bath having a temperature of 140° C., and the pressure in the flask was gradually reduced to about 90 kPa while stirring the contents of the flask. Then, the pressure in the flask was further reduced to 85 kPa while stirring the contents of the flask and withdrawing a distillate from the flask, and a reaction was performed under 85 kPa for 12 hours while further withdrawing a distillate from the flask. Subsequently, unreacted components (such as an unreacted alcohol) in the flask were distilled off from the flask over 30 minutes while gradually reducing the pressure in the flask to about 200 Pa. The flask was taken out from the oil bath, and the inside of the flask was cooled. Then, nitrogen gas was introduced into the flask to elevate the pressure in the flask to atmospheric pressure. By the above-mentioned operation, 127 g of a viscous liquid was obtained.

The distillate withdrawn from the flask was analyzed. As a result, it was found that the distillate contained about 260 mmol of water. The above-obtained viscous liquid was analyzed by $^1$H—, $^{13}$C— and $^{119}$Sn-NMR's.

As a result, it was found that the viscous liquid contained dibutyltin bis(3-methylbutoxide), 1,1,3,3-tetrabutyl-1,3-di (3-methylbutoxy)distannoxane and tributyltin(3-methylbutoxide).

Step (1)

114 g of the above-obtained viscous liquid was charged into a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having a pressure of 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken out and analyzed. As a result, it was found that the reaction mixture obtained 1 hour after the start of the reaction contained di(3-methylbutyl)carbonate in a yield of 18%, and that the reaction mixture obtained 4 hours after the start of the reaction contained di(3-methylbutyl) carbonate in a yield of 20.4%.

After the reaction, the inside of the autoclave was allowed to cool, and carbon dioxide gas was purged therefrom.

Step (2)

After step (1), the contents of the autoclave were allowed to cool to room temperature (about 20° C.). Then, the autoclave was opened to recover the reaction mixture therefrom. The reaction mixture was charged into a 300-ml eggplant-shaped flask equipped with a cooling tube, a vacuum pump and a vacuum controller (manufactured and sold by Okano Works, Ltd., Japan). Further, a stirrer was placed in the flask. Then, the flask was immersed in an oil bath having a temperature of 140° C.

A distillation was performed at 140° C. while stirring the contents of the flask and gradually reducing the pressure in the flask. During the distillation, 3-methyl-1-butanol was first distilled off from the flask and, then, di(3-methylbutyl)carbonate was distilled off from the flask. By the distillation, about 9 g of di(3-methylbutyl)carbonate and about 1 mmol of tributyltin(3-methylbutoxide) were obtained.

Step (3)

Into a 1-liter four-necked flask equipped with a cooling tube (which was connected with a vacuum controller and a vacuum pump) and a Dean-Stark trap were charged the distillation residue obtained in step (2) above and 502 g (5.7 mol) of 3-methyl-1-butanol (manufactured and sold by Aldrich, U.S.A.). Further, a stirrer was placed in the flask.

The flask was immersed in an oil bath having a temperature of 140° C., and the pressure in the flask was gradually reduced to about 90 kPa while stirring the contents of the flask. Then, the pressure in the flask was further reduced to 85 kPa while stirring the contents of the flask and withdrawing a distillate from the flask, and a reaction was performed under 85 kPa for 20 hours while further withdrawing a distillate from the flask. Thereafter, unreacted components (such as an unreacted alcohol) in the flask were distilled off from the flask over 30 minutes while gradually reducing the pressure in the flask to about 200 Pa, thereby obtaining a reaction mixture. The reaction mixture was analyzed by 1H—, 13C— and 119Sn-NMR's. As a result, it was found that the reaction mixture contained dibutyltin bis(3-methylbutoxide) and 1,1,3,3-tetrabutyl-1,3-di(3-methylbutoxy)distannoxane. Further, the reaction mixture also contained about 2 mmol of tributyltin (3-methylbutoxide). Subsequently, the temperature of the oil bath was lowered so that the internal temperature of the flask became about 93° C., and a distillate was removed from the flask under a pressure of 50 Pa. Then, the flask was taken out from the oil bath, and the inside of the flask was cooled. Then, nitrogen gas was introduced into the flask to elevate the pressure in the flask to atmospheric pressure. By this operation, 110 g of a viscous liquid was obtained.

The above-obtained viscous liquid was analyzed by 1H—, 13C— and $^{119}$Sn-NMR's. As a result, it was found that the viscous liquid contained dibutyltin bis(3-methylbutoxide)

and 1,1,3,3-tetrabutyl-1,3-di(3-methylbutoxy)distannoxane. It was also found that about 1 mmol of tributyltin(3-methylbutoxide) was distilled off.

Step (1)

112 g of the above-obtained viscous liquid was charged into a 200-ml autoclave (manufactured and sold by Toyo Koatsu Co., Ltd., Japan) which had a carbon dioxide gas bomb connected thereto through a SUS tube and a valve. The autoclave was sealed, and the atmosphere in the autoclave was purged with nitrogen gas. Then, the above-mentioned valve was opened to introduce carbon dioxide gas having a pressure of 5 MPa into the autoclave. The introduction of carbon dioxide gas into the autoclave was performed for 10 minutes while stirring the contents of the autoclave, and, then, stopped by closing the valve of the carbon dioxide gas bomb. Subsequently, the internal temperature of the autoclave was elevated to 120° C. while stirring. Then, a reaction was performed for 4 hours while maintaining the internal pressure of the autoclave at about 4 MPa.

During and after the reaction, samples of the reaction mixture in the autoclave were taken out and analyzed. As a result, it was found that the reaction mixture obtained 1 hour after the start of the reaction contained di(3-methylbutyl)carbonate in a yield of 18%, and that the reaction mixture obtained 4 hours after the start of the reaction contained di(3-methylbutyl)carbonate in a yield of 20.4%.

After the reaction, the inside of the autoclave was allowed to cool, and carbon dioxide gas was purged therefrom.

Step (2)

After step (1), the contents of the autoclave were allowed to cool to room temperature (about 20° C.). Then, the autoclave was opened to recover the reaction mixture therefrom. The reaction mixture was charged into a 300-ml eggplant-shaped flask equipped with a cooling tube, a vacuum pump and a vacuum controller (manufactured and sold by Okano Works, Ltd., Japan). Further, a stirrer was placed in the flask. Then, the flask was immersed in an oil bath having a temperature of 140° C.

A distillation was performed at 140° C. while stirring the contents of the flask and gradually reducing the pressure in the flask. During the distillation, 3-methyl-1-butanol was first distilled off from the flask and, then, di(3-methylbutyl)carbonate was distilled off from the flask. By the distillation, about 9 g of di(3-methylbutyl)carbonate and about 1 mmol of tributyltin(3-methylbutoxide) were obtained.

Step (3)

Into a 1-liter four-necked flask equipped with a cooling tube (which was connected with a vacuum controller and a vacuum pump) and a Dean-Stark trap were charged the distillation residue obtained in step (2) above, 502 g (5.7 mol) of 3-methyl-1-butanol (manufactured and sold by Aldrich, U.S.A.) and 1 g (4 mmol) of dibutyltin oxide. Further, a stirrer was placed in the flask.

The flask was immersed in an oil bath having a temperature of 140° C., and the pressure in the flask was gradually reduced to about 90 kPa while stirring the contents of the flask. Then, the pressure in the flask was further reduced to 85 kPa while stirring the contents of the flask and withdrawing a distillate from the flask, and a reaction was performed under 85 kPa for 20 hours while further withdrawing a distillate from the flask. Thereafter, unreacted components (such as an unreacted alcohol) in the flask were distilled off from the flask over 30 minutes while gradually reducing the pressure in the flask to about 200 Pa, thereby obtaining a viscous reaction mixture. The viscous reaction mixture was analyzed by $^1$H—, $^{13}$C— and $^{119}$Sn-NMR's. As a result, it was found that the reaction mixture contained dibutyltin bis(3-methylbutoxide) and 1,1,3,3-tetrabutyl-1,3-di(3-methylbutoxy)distannoxane. Further, the reaction mixture also contained about 2 mmol of tributyltin(3-methylbutoxide). Subsequently, the temperature of the oil bath was lowered so that the internal temperature of the flask became about 93° C., and a distillate was removed from the flask under a pressure of 50 Pa. The flask was taken out from the oil bath, and the inside of the flask was cooled. Then, nitrogen gas was introduced into the flask to elevate the pressure in the flask to atmospheric pressure. By this operation, 110 g of a viscous liquid was obtained.

The above-obtained viscous liquid was analyzed by $^1$H—, $^{13}$C— and $^{119}$Sn-NMR's. As a result, it was found that the viscous liquid contained dibutyltin bis(3-methylbutoxide) and 1,1,3,3-tetrabutyl-1,3-di(3-methylbutoxy)distannoxane. It was also found that about 1 mmol of tributyltin(3-methylbutoxide) was distilled off.

INDUSTRIAL APPLICABILITY

By the method of the present invention, a carbonic ester can be produced in high yield from an organometal compound having in its molecule at least two metal-oxygen-carbon linkages and carbon dioxide. It is advantageous that carbon dioxide has neither toxicity nor corrosiveness and is inexpensive. Further, the method of the present invention is advantageous not only in that the organometal compound after use in this method can be regenerated and recycled in the method, but also in that an unregenerable unreactive organometal compound formed can be removed from the reaction system, thereby realizing an effective and stable production of a carbonic ester. Further, there is no need for the use of a large amount of a dehydrating agent, thereby preventing occurrence of wastes derived from the dehydrating agent. Therefore, the method of the present invention is commercially very useful and has high commercial value.

The invention claimed is:

1. A method for producing a carbonic ester of a formula RO(CO)OR, wherein R represents an unsaturated or saturated hydrocarbon group, comprising the steps of:
   (1) performing a reaction between a first organometal compound mixture and carbon dioxide, said first organometal compound mixture comprising a mixture of a reactive organometal compound having in its molecule at least two metal-oxygen-carbon linkages and an unregenerable unreactive compound which is derived from said reactive organometal compound and which has in its molecule at least three metal-carbon linkages, wherein said reactive organometal compound comprises at least one compound selected from the group consisting of:
   an organometal compound represented by the formula (1):

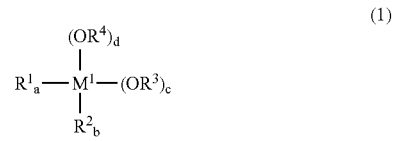

wherein:

$M^1$ represents a metal atom selected from the group consisting of elements belonging to Groups 4 and 14 of the Periodic Table, exclusive of silicon;

each of $R^1$ and $R^2$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

$R^3$ and $R^4$ are the same and represent a straight chain or branched $C_1$-$C_{12}$ alkyl group, a $C_5$-$C_{12}$ cycloalkyl group, a straight chain or branched $C_2$-$C_{12}$ alkenyl group, or a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl; and each of a and b is an integer of from 0 to 2, a+b=0 to 2, each of c and d is an integer of from 0 to 4, and a+b+c+d=4; and an organometal compound represented by the formula (2):

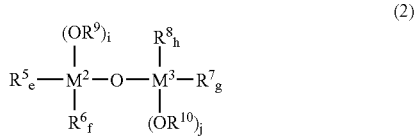

(2)

wherein:

each of $M^2$ and $M^3$ independently represents a metal atom selected from the group consisting of elements belonging to Groups 4 and 14 of the Periodic Table, exclusive of silicon;

each of $R^5$, $R^6$, $R^7$ and $R^8$ independently represents a straight chain or branched $C_1$-$C_{12}$ alkyl group, a $C_5$-$C_{12}$ cycloalkyl group, a straight chain or branched $C_2$-$C_{12}$ alkenyl group, a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl, or an unsubstituted or substituted $C_6$-$C_{20}$ aryl group;

$R^9$ and $R^{10}$ are the same as $R^3$ and $R^4$; and each of e, f, g and h is an integer of from 0 to 2, e+f=0 to 2, g+h=0 to 2, each of i and j is an integer of from 1 to 3, e+f+i=3, and g+h+j=3, to thereby obtain a reaction mixture containing a carbonic ester formed by the reaction, said unregenerable unreactive compound, and a regenerable metamorphic organometal compound derived from said reactive organometal compound, (2) separating said reaction mixture into a first portion containing said carbonic ester and said unregenerable unreactive compound, and a second portion containing said regenerable metamorphic organometal compound, and (3) reacting said second portion of said reaction mixture with a first alcohol to form a second organometal compound mixture and water and removing said water from said second organometal compound mixture, said second organometal compound mixture comprising a mixture of a reactive organometal compound having in its molecule at least two metal-oxygen-carbon linkages and an unregenerable unreactive compound which is derived from said reactive organometal compound and which has in its molecule at least three metal-carbon linkages.

2. The method according to claim 1, which further comprises, after step (3), a step (4) in which said second organometal compound mixture obtained in step (3) is recovered and recycled to step (1).

3. The method according to claim 1 or 2, wherein $R^3$ and $R^4$ in formula (1) and $R^9$ and $R^{10}$ in formula (2) represent an n-butyl group, an isobutyl group, a straight chain or branched $C_5$-$C_{12}$ alkyl group, or a straight chain or branched $C_4$-$C_{12}$ alkenyl group.

4. The method according to claim 1 or 2, wherein each of $M^1$ in formula (1) and $M^2$ and $M^3$ in formula (2) represents a tin atom.

5. The method according to claim 1 or 2, wherein said reactive organometal compound used in step (1) is produced from an organotin oxide and an alcohol.

6. The method according to claim 1 or 2, wherein, in step (1), said reactive organometal compound is used in at least one form selected from the group consisting of a monomeric form, an oligomeric form, a polymeric form and an associated form.

7. The method according to claim 1 or 2, wherein, in step (1), said reactive organometal compound is used in an amount which is 1/50 to 1 time the stoichiometric amount relative to the amount of said carbon dioxide.

8. The method according to claim 1 or 2, wherein said reaction in step (1) is performed at 20° C. or higher.

9. The method according to claim 1 or 2, wherein, in step (2), said separation of said reaction mixture into said first portion and said second portion is performed by at least one separation method selected from the group consisting of distillation, extraction and filtration.

10. The method according to claim 1 or 2, wherein said first alcohol used in step (3) is at least one alcohol selected from the group consisting of an alkyl alcohol having a straight chain or branched $C_1$-$C_{12}$ alkyl group, a cycloalkyl alcohol having a $C_5$-$C_{12}$ cycloalkyl group, an alkenyl alcohol having a straight chain or branched $C_2$-$C_{12}$ alkenyl group, and an aralkyl alcohol having a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl.

11. The method according to claim 10, wherein said first alcohol has a boiling point which is higher than the boiling point of water, as measured under atmospheric pressure.

12. The method according to claim 11, wherein said first alcohol is at least one alcohol selected from the group consisting of 1-butanol, 2-methyl-1-propanol, an alkyl alcohol having a straight chain or branched $C_5$-$C_{12}$ alkyl group, an alkenyl alcohol having a straight chain or branched $C_4$-$C_{12}$ alkenyl group, a cycloalkyl alcohol having a $C_5$-$C_{12}$ cycloalkyl group, and an aralkyl alcohol having a $C_7$-$C_{20}$ aralkyl group comprised of unsubstituted or substituted $C_6$-$C_{19}$ aryl and alkyl selected from the group consisting of straight chain or branched $C_1$-$C_{14}$ alkyl and $C_5$-$C_{14}$ cycloalkyl.

13. The method according to claim 1 or 2, wherein said removal of said water in step (3) is performed by membrane separation.

14. The method according to claim 13, wherein said membrane separation is pervaporation.

15. The method according to claim 1 or 2, wherein said removal of said water in step (3) is performed by distillation.

* * * * *